United States Patent
Fedele et al.

(10) Patent No.: US 7,952,697 B2
(45) Date of Patent: May 31, 2011

(54) COFFEE REFRACTOMETER METHOD AND APPARATUS

(75) Inventors: Vincent Fedele, Acton, MA (US); Philip Gaudet, Rockport, ME (US); Daniel Henri Raguin, Acton, MA (US)

(73) Assignee: Voice Systems Technology, Inc., Harvard, MA (US)

( * ) Notice: Subject to any disclaimer, the term of this patent is extended or adjusted under 35 U.S.C. 154(b) by 147 days.

(21) Appl. No.: 12/247,232

(22) Filed: Oct. 8, 2008

(65) Prior Publication Data

US 2010/0085560 A1    Apr. 8, 2010

(51) Int. Cl.
G01N 21/41    (2006.01)
(52) U.S. Cl. ...................................... 356/134
(58) Field of Classification Search .................. 356/134
See application file for complete search history.

(56) References Cited

U.S. PATENT DOCUMENTS

| | | | |
|---|---|---|---|
| 3,640,727 | A | 2/1972 | Heusinkveld |
| 4,988,590 | A | 1/1991 | Price |
| 5,355,211 | A | 10/1994 | Thompson |
| 5,582,717 | A | 12/1996 | Di Santo |
| 5,721,005 | A | 2/1998 | Gutwein |
| 6,034,762 | A | 3/2000 | Cotton |
| 6,808,731 | B1 | 10/2004 | Gutwein |
| 7,369,221 | B2 | 5/2008 | Amamiya |
| 7,492,447 | B2 | 2/2009 | Nakajima |
| 2004/0145731 | A1 | 7/2004 | Nakajima |
| 2004/0177762 | A1 | 9/2004 | Gutwein |
| 2005/0103202 | A1 | 5/2005 | Rahn |
| 2006/0196363 | A1 | 9/2006 | Rahn |
| 2008/0001105 | A1 | 1/2008 | Chiarello |
| 2008/0282897 | A1* | 11/2008 | Webster et al. ............... 99/280 |

FOREIGN PATENT DOCUMENTS

| | | |
|---|---|---|
| DE | 10350747 A1 | 5/2004 |
| EP | 0554008 A2 | 8/1993 |
| EP | 1637055 A2 | 3/2006 |
| EP | 1875807 A1 | 1/2008 |

(Continued)

OTHER PUBLICATIONS

Adler Coffeegeek—"Measuring Coffee Strength With a Brix Meter", Downloaded from the Internet: URL:http://coffeegeek.com/forums/coffee/machines/372185?LastView+1227065615&Page+1> (retrieved on Jan. 27, 2010) (Jan. 16, 2006).

(Continued)

Primary Examiner — Roy Punnoose
(74) Attorney, Agent, or Firm — Mark P Kahler

(57) ABSTRACT

A coffee refractometer includes a prism that receives a brewed coffee sample, thus forming a prism-sample interface. A processor or microcontroller controls a light source to provide incident light to the prism-sample interface. The prism-sample interface refracts light toward a photodetector. A temperature sensor provides temperature information to the processor. The refractometer includes a memory store that stores a TDS formula that expresses the TDS of brewed coffee as a function of the index of refraction ($n_s$) of brewed coffee and the temperature of brewed coffee. The processor determines the TDS of the brewed coffee sample by accessing the TDS formula in the memory store and employing the determined index of refraction ($n_s$) of the brewed coffee sample to find the TDS from the TDS formula. The refractometer displays the resultant TDS % on a display of the refractometer and/or transmits such information to an information handling system.

16 Claims, 30 Drawing Sheets

FOREIGN PATENT DOCUMENTS

GB               2111377 A       7/1983

OTHER PUBLICATIONS

ATAGO1—"Automatic Digital Refractometers RX-CX Series" (downloaded from www.atago.net/english/images/catalog/RX-alpha_e.pdf on Aug. 12, 2008).

ATAGO2—"Digital Hand-held "Pocket" Refractometer PAL Special Scales" (downloaded from www.atago.net/english/products_palsp.php on Feb. 23, 2010).

BRIX—"Brix" (downloaded from http://en.wikipedia.org/wiki/Brix on Aug. 31, 2008).

BS Bellingham & Stanley RFM 81 Automatic for Sale—"Bellingham & Stanley Automatic Refractometer RFM 8" (downloaded from http://www.labx.com/v2/adsearch/Detail3.cfm?adnumb=366291 on Sep. 1, 2008).

CB PUB—"The Direct Reading Coffee Hydrometer" Publication No. 61, The Coffee Brewing Center (1970).

Cole-Parmer—"Refractometers" (downloaded from URL http://www.coleparmer.com/techinfo/techinfo.asp?htmlfile=Refractometers.htm&ID=633 on Sep. 24, 2008).

Hanson—"Refractometry: Theory, Analyzing Results" (downloaded from http://www2.ups.edu/faculty/hanson/labtechniques/refractometry/interpret.htm on Sep. 24, 2008).

Lingle—"The Basics of Brewing Coffee" Coffee Brewing Handbook, Speciality Coffee Association of America, ISBN 1-882552-03-2 (1996).

Lockhart—"The Soluble Solids in Beverage Coffee As An Index To Cup Quality" Publication No. 27, The Coffee Brewing Center (1969).

Paselk—"The Evolution of the Abbe Refractometer" (downloaded from http://www.humboldt.edu/%7Escimus/Essays/EvolAbbeRef/EvolAbbeRef.htm on Jun. 1, 2008).

Philiplaven—"Refractive index as a function of wavelength" (downloaded from http://www.philiplaven.com/p20.html on Jun. 1, 2008).

REICHERT1—"AR200 Refractometer User's Guide" (downloaded from www.reichert.com Feb. 1, 2010).

REICHERT2—"Reichert r2mini Digital Refractomer Brochure" (Oct. 2008).

REICHERT3—"r2mini Refractometer User Guide" (downloaded from www.reichert.com Feb. 1, 2010).

SCAA1—"SCAA Shop Technical Tools" (downloaded from http://www.scaa.org/shop/product_detail.asp?productid=R400300 on Sep. 19, 2008).

SCAA2—"Coffee Brewing Control Chart Brewing Ratio: Grams per Liter", Specialty Coffee Association of America (1966).

SCAA3—"Coffee Brewing Control Chart Brewing Ratio: Grams per 6.0 fl. oz. per Cup", Specialty Coffee Association of America (1966).

SCAA4—"Coffee Brewing Control Chart Brewing Ratio: Ounces per Half-Gallon", Specialty Coffee Association of America (1968).

SCAI—"SCAE Gold Cup Training Filter Brewing for Brewmaster's", Speciality Coffee Assn. of Europe, Coffee Fiesta, Antwerp (2007).

SCIENCECO—Automatic Digital Refractometer, Atago RX-007 (downloaded from http://secure.sciencecompany.com/Automatic-Digital-Refractometer-Atago-RX-007-alpha-P16117C688.aspx on Aug. 12, 2008).

TOPAC—"Brix Refractometers" (downloaded from http://www.topac.com/refractPR101.html on Aug. 31, 2008).

Pope R D—"Pulse brew and Pre-infusion", Tea & Coffee Asia, vol. Q1, pp. 54-56, XP002567632 (Mar. 2008).

Thormalen—"Refractive Index of Water and Its Dependence on Wavelength, Temperature, and Density", J. Phys. Chem. Ref. Data, vol. 14, No. 4, XP002567322 (1985).

PCT Search Report and Opinion—PCT/US2009/059588, International Filing Date May 10, 2009.

PCT Search Report and Opinion—PCT/US2009/059593, International Filing Date May 10, 2009.

Bellingham—"Refractive Index & Brix Temperature Relationship", Bellingham & Stanley Sheet (2007).

Kernchen—"ABBEMAT High Performance Automatic Refractometers", (2003).

Madsen—Message from the President, ICUMSA News 39 (2000).

Pollach—Method of Particle Size Evaluation (2004, 2006).

Reichert—Instruction Manual—Brix Scale (2003).

\* cited by examiner

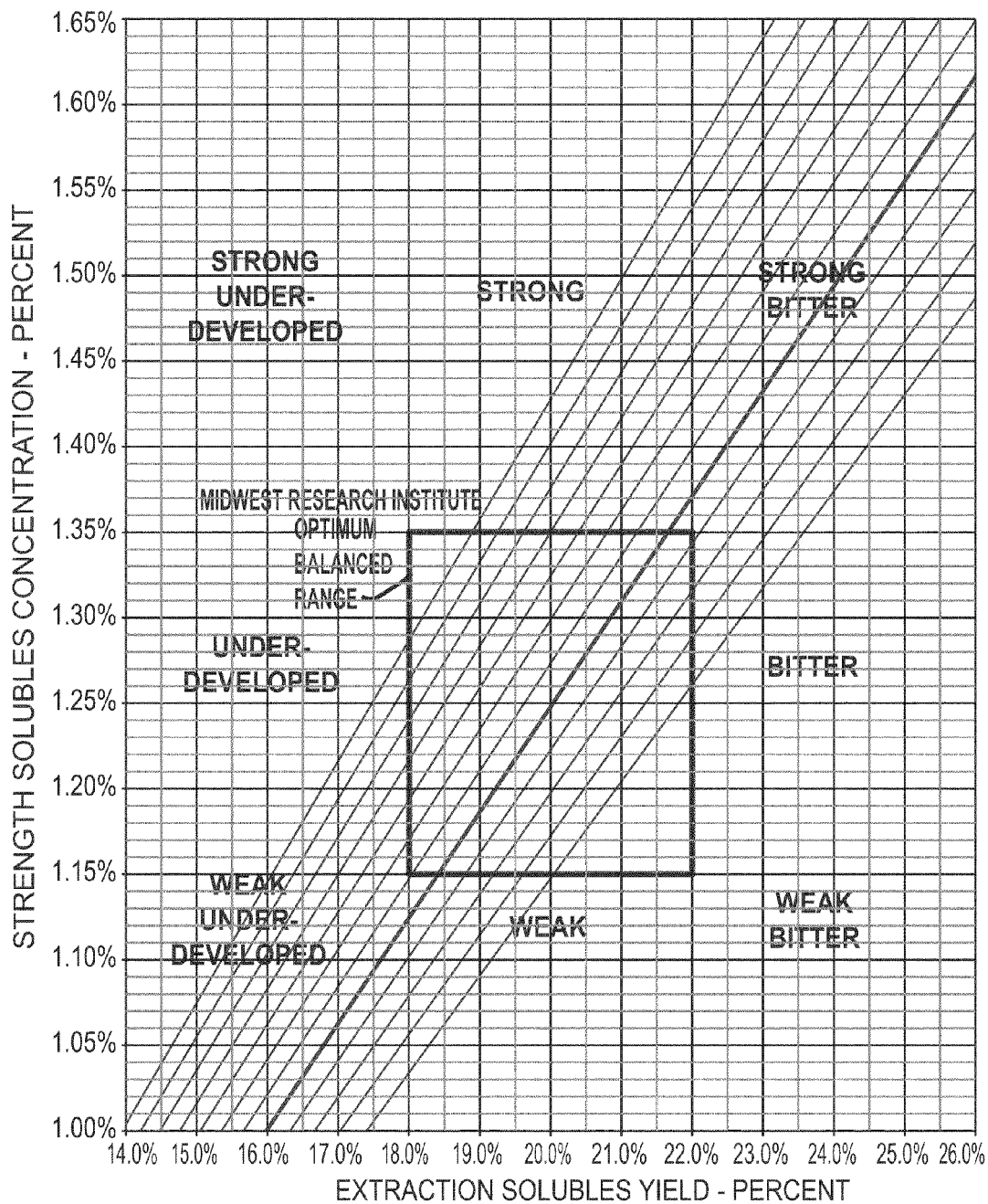

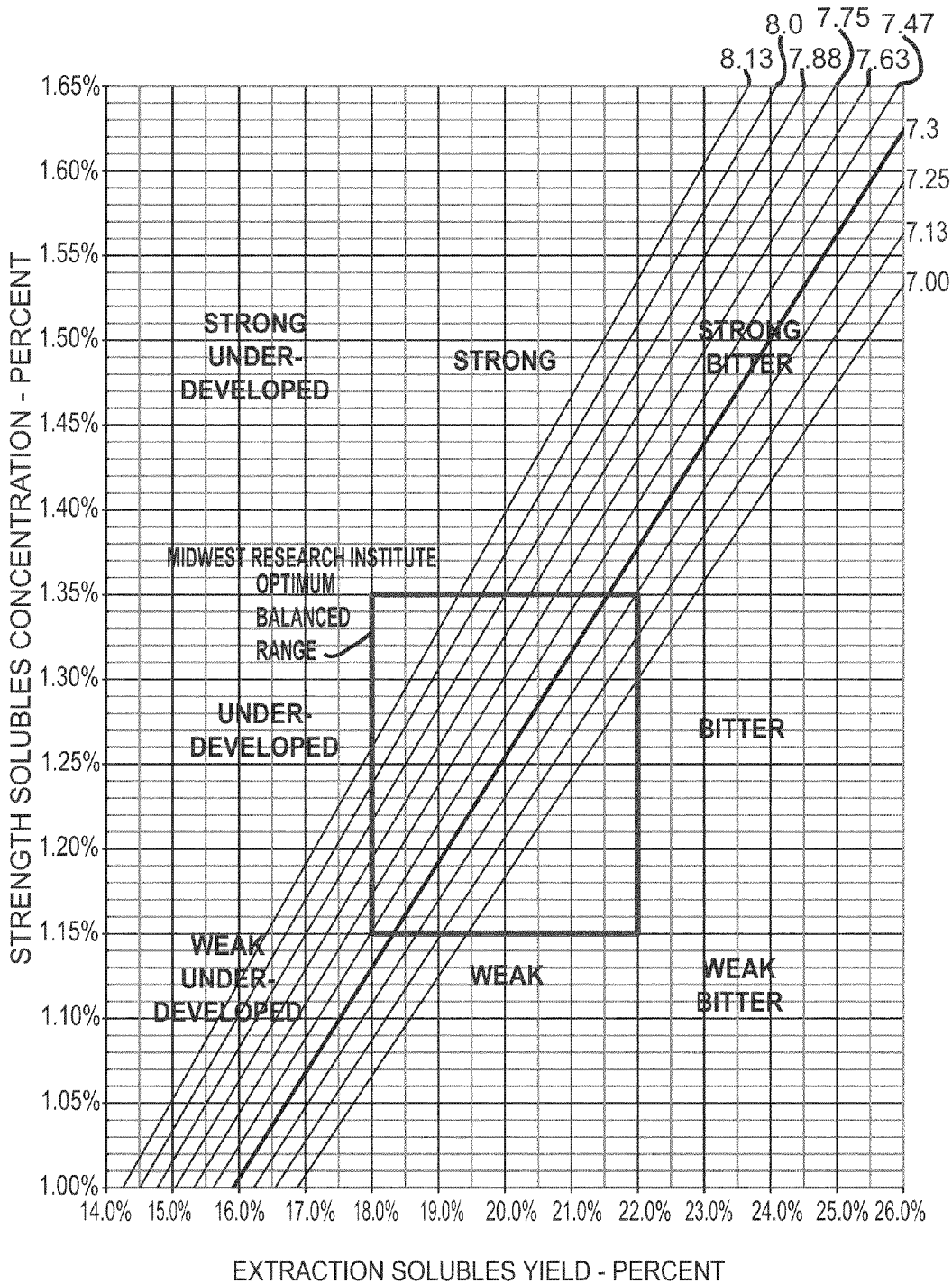
FIG. 4C (PRIOR ART) COFFEE BREWING CONTROL CHART
OUNCES COFFEE PER 1.0 GALLON WATER

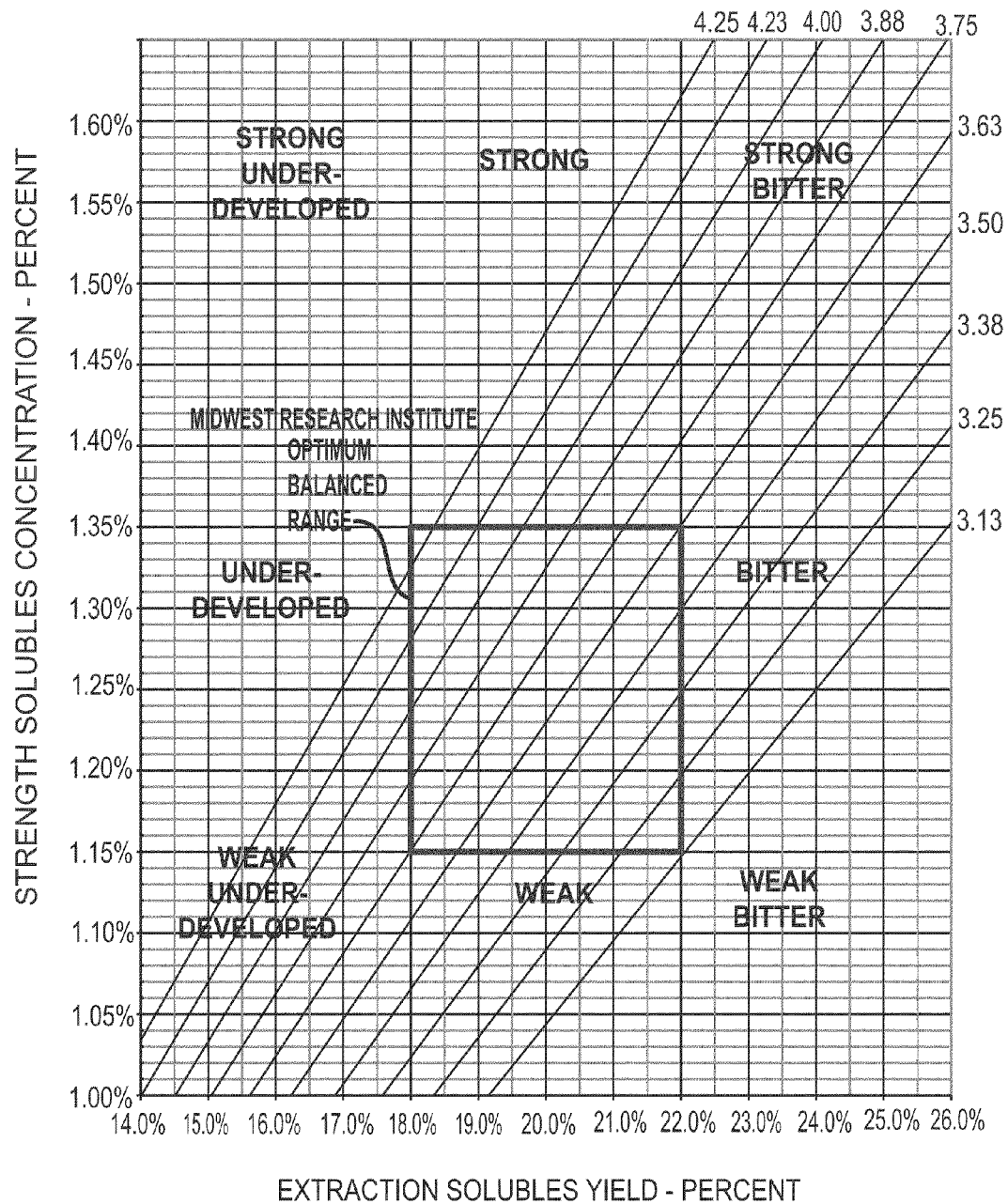

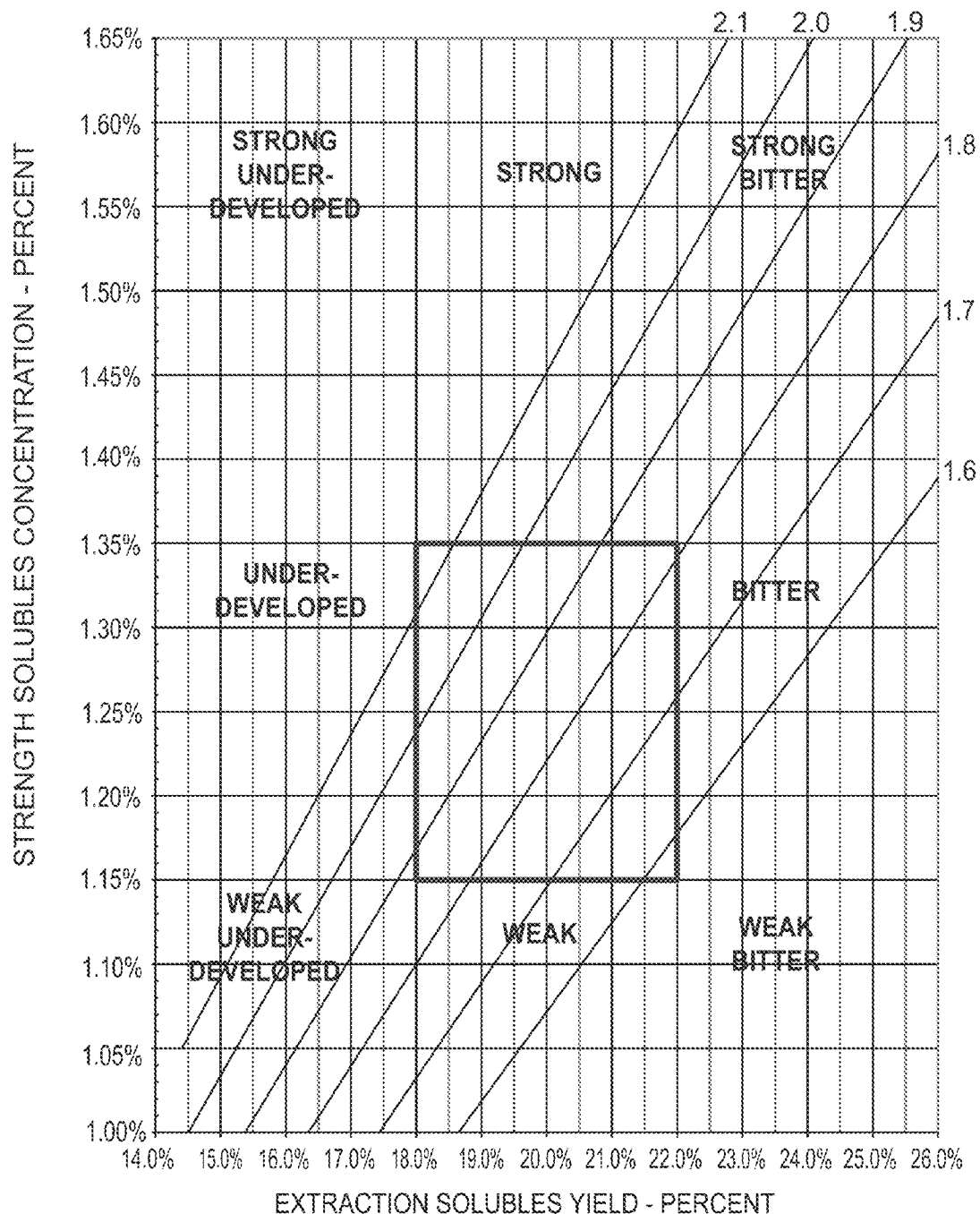
FIG. 4E (PRIOR ART) COFFEE BREWING CONTROL CHART
OUNCES COFFEE PER 1.0 GALLON WATER

FIG. 7B

| | | |
|---|---|---|
| COFFEE DESIGN AND MEASUREMENT PROCESS FLOW CHART - CONTINUED | | |
| TAKE TDS MEASUREMENT | | |
| 715 | CALIBRATE ATAGO PAL-COFFEE REFRACTOMETER | USING DISTILLED WATER, REFRACTOMETER & WATER SHOULD BE AT 20-25 DEG C |
| | COOL 20 ML SAMPLE OF BREWED COFFEE" | TO 20-30 DEG C |
| | PLACE SAMPLE | IN COFFEE REFRACTOMETER |
| | ALLOW 1-2 MINUTES | FOR SAMPLE AND REFRACTOMETER TO REARCH SAME TEMP |
| | TAKE TDS READING | PRES START ON ATAGO PAL-COFFEE REFRACTOMETER |
| | ENTER TDS READING | IN THE DISSOLVED SOLIDS MEASURMENT BOX |
| | USING PAL-COFFEE REFRACTOMETER | ENTER VALUE IN % TDS |
| | IF USING COFFEE CONDUCTIVITY METER | ENTER VALUE IN PPM (ACCURACY MAY BE DEGRADED) |
| | IF USING BRIX REFRACTOMETER | ENTER VALUE IN % OR DEG BRIX (ACCURACY MAY BE DEGRATED) |
| | BREW RESULT IS PLOTED IN BLUE | |
| | CORRECT BREW PROTOCOL IF NEEDED, BASED ON OVER OR UNDER EXTRACTION FROM TARGET | |
| SAVE DATA 720 | SAVE DATA | |
| | SAVE PLOT | |
| | RECALL PREVIOUS COFFEE RECIPE | |
| | EMAIL DATA | |
| PRINT DATA 725 | PRINT CHART | |
| | PRANT DATA | |
| HELP INFO 730 | EXTRACTMOJO USER MANUAL | ADOBE READER FORMAT IN PDF ONLINE FROM HELP MENU |
| | EXTRACTMOJO QUICKSTART GUIDE | ADOBE READER FORMAT IN PDF ONLINE FROM HELP MENU |
| | EXTRACTMOJO LICENSE AGREEMENT | ADOBE READER FORMAT IN PDF ONLINE FROM HELP MENU |
| | EXTRACTMOJO WEB SITE | EXTRACTMOJO SUPPORT SITE AND FUTURE FORUM (REQUIRES THE LIVE NETWORK CONNECTION) |
| ABOUT 735 | EXTRACTMOJO CREDITS | THREE BEAN TREE SOFTWARE DEVELOPERS AND BETA TESTERS |
| | EXTRACTMOJO NOTICES | TRADEMARK NOTICE |
| | EXTRACTMOJO LICENSE KEY | KEY IS REQUIRED WHEN COMMUNICATING WITH GHC FOR ALL TECHNICAL SUPPORT |

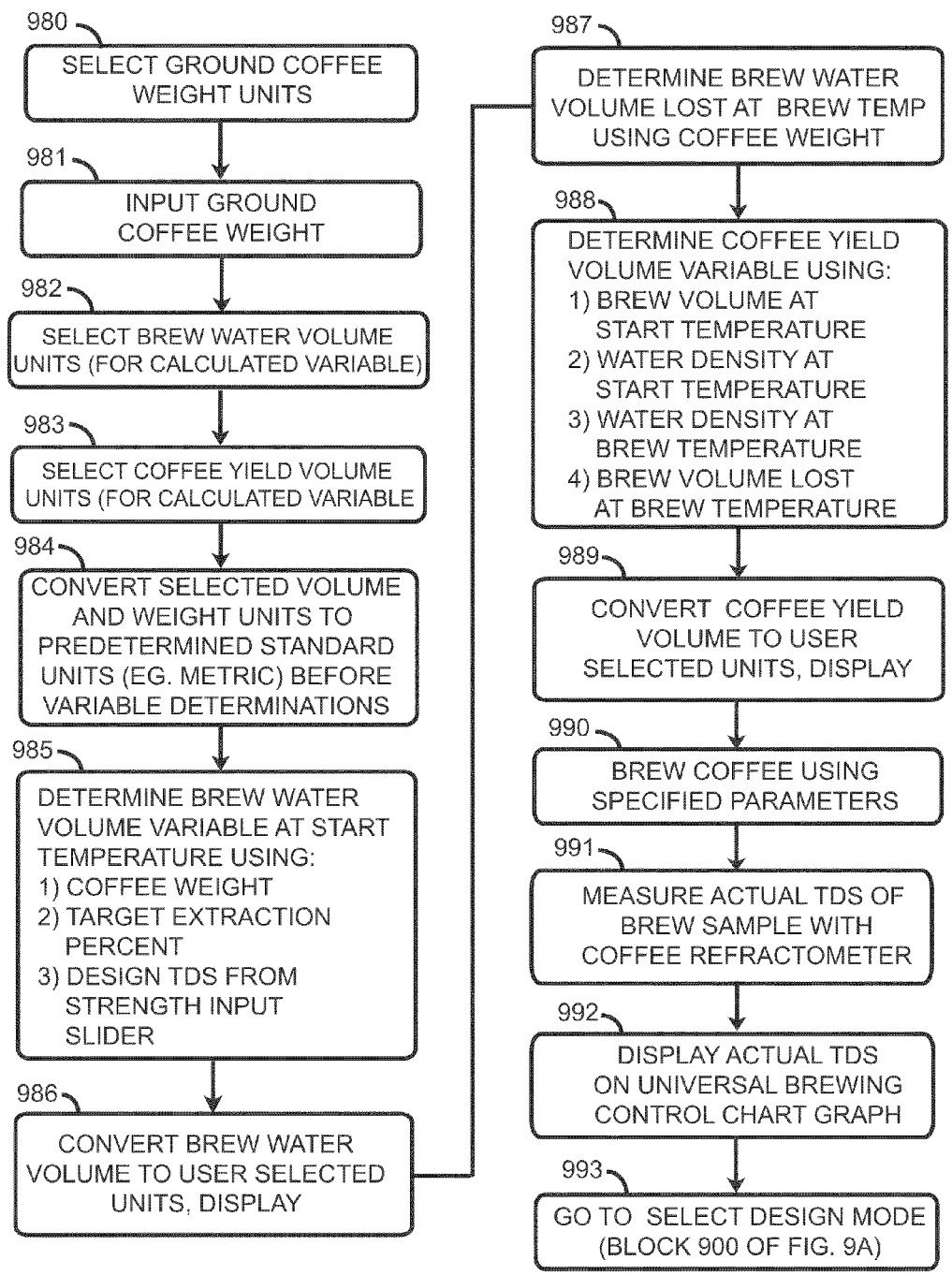

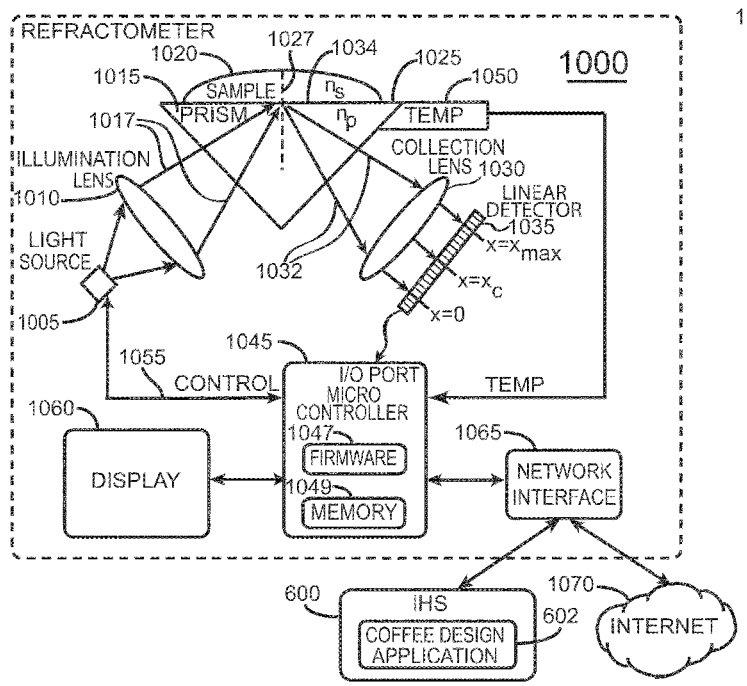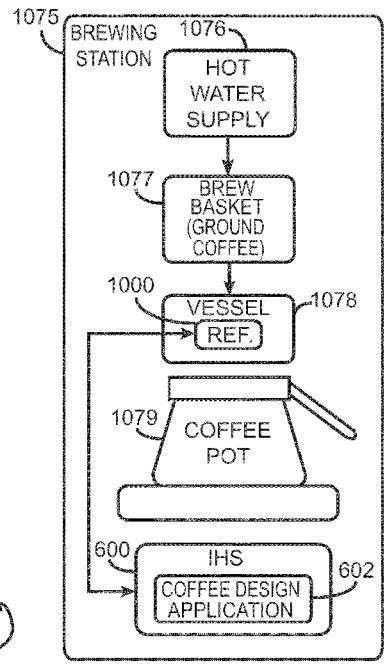
FIG. 10A
FIG. 10B

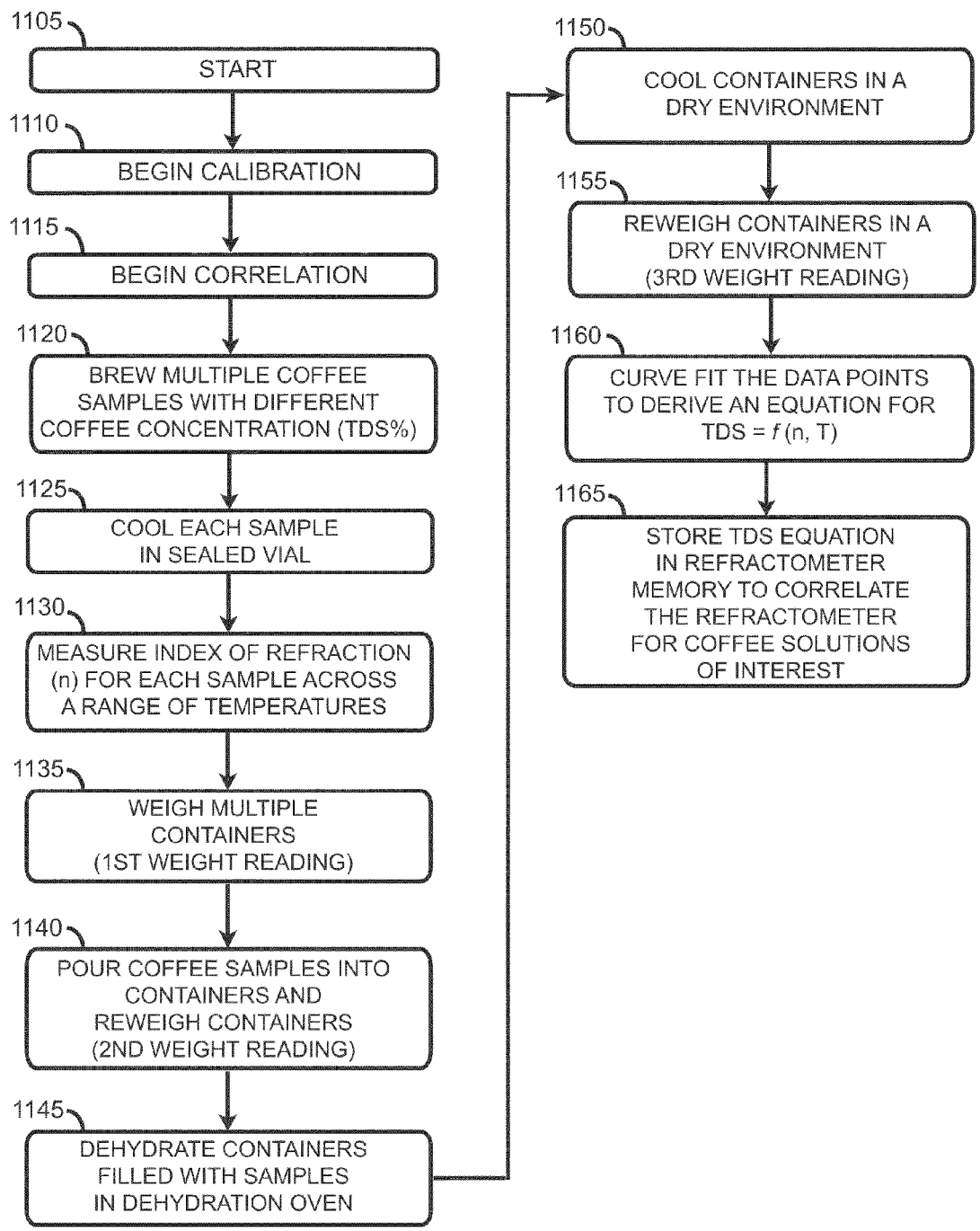

METHOD OF TAKING A TDS% READING OF A COFFEE BREW SAMPLE WITH THE REFRACTOMETER

COFFEE REFRACTOMETER METHOD AND APPARATUS

RELATED PATENT APPLICATIONS

This patent application relates to the U.S. patent application by Fedele, et al., entitled "METHOD AND APPARATUS FOR BREWING COFFEE VIA UNIVERSAL COFFEE BREWING CHART GENERATION", application Ser. No. 12/247,231, filed Oct. 8, 2008, which is assigned to the same assignee as the subject patent application and which is incorporated herein by reference in its entirety.

TECHNICAL FIELD OF THE INVENTION

The disclosures herein relate generally to the preparation of beverages for consumption, and more particularly, to brewing beverages such as coffee.

BACKGROUND

Quality standards in the specialty coffee industry established during the 1950's and 1960's that coffee extraction of approximately 20% (usually a range of ~18-22%) will achieve the best quality brewed coffee, using various brew methods. Over the ensuing years these established standards have been generally referred to as the gold-cup standard, and have been accepted internationally by many institutions, educational establishments, and standards committees. The precise extraction (solubles yield) and strength (solubles concentration) may be varied for particular coffees, to achieve finely tuned recipes for particular coffee cultivars, climates and growing regions, also known as terroir, and other characteristics.

Extraction (solubles yield) refers to the percentage of the dry coffee by weight that is removed by dissolving in water during the brewing process. Up to 30% of the available soluble solids in ground coffee can be extracted, with most of the remaining 70% being cellulose, and not soluble in water. However, generally speaking, extracting more than 22% will begin to sharply increase those components in coffee that contribute to the bitter taste defects associated with over-extraction. Extracting less than 18% is generally associated with weak, under-developed taste defects.

The finished brew is a balance between extraction (solubles yield) and strength (solubles concentration). Over-extracting results in the extraction of many of the bitter components of the remaining solids. These contribute significantly to those taste defects known as bitter, strong-bitter and weak bitter. Under-extracting causes a taste defect that is under-developed and can be weakly or strongly under-developed. As coffee dissolves, the bulk of the solids including the sweeter components dissolve during the first 30-50% of the brewing cycle, and the more bitter elements start to dissolve in the latter half of the brewing cycle. The highest quality coffee will have rich aroma, fullness of body, delicacy of flavor as well as clarity and unique character—all optimally balanced. Achieving these attributes requires a significant degree of precision during the coffee brewing process.

Strength (solubles concentration) refers to the measured amount of solids extracted into the final coffee solution. Strength may be expressed as the percentage total dissolved solids (% TDS). For example, for 100 grams of a coffee measuring 1.3% TDS, there are 98.7 grams of water, and 1.3 grams of dissolved coffee solids in solution.

Refractive index measurements have been used for process control in the food industry since the 1940s. Typical measurements are usually for sugars in fruits such as melons, for orange and other juices, for sugar content in grapes for the wine industry, and many other examples.

SUMMARY

Accordingly, in one embodiment a method of determining the total dissolved solids (TDS) in brewed coffee is disclosed. The method includes providing a brewed coffee sample to a coffee refractometer. The method also includes determining, by the coffee refractometer, the index of refraction ($n_s$) of the brewed coffee sample. The method further includes determining, by the coffee refractometer, the temperature of the brewed coffee sample to provide temperature compensation to the coffee refractometer. The method still further includes accessing, by a processor in the refractometer, a memory store in the refractometer, the memory store including a TDS formula that expresses the TDS of brewed coffee as a function of the index of refraction ($n_s$) of brewed coffee and the temperature of brewed coffee, to determine the resultant TDS of the brewed coffee sample.

In another embodiment, a coffee refractometer is disclosed. The coffee refractometer includes a prism for receiving a brewed coffee sample thereon to form a prism-sample interface. The coffee refractometer also includes a processor that controls a light source to provide incident light to the prism-sample interface, the prism-sample interface refracting light toward a photodetector that couples to the processor. The coffee refractometer further include a temperature sensor, situated adjacent the prism-sample interface and coupled to the processor, that provides temperature information to the processor. The coffee refractometer still further includes a memory store, accessible by the processor, that stores a TDS formula that expresses the TDS of brewed coffee as a function of the index of refraction ($n_s$) of brewed coffee and the temperature of brewed coffee, to determine the resultant TDS of the brewed coffee sample.

In one embodiment, the TDS formula expresses TDS as a linear function of index of refraction ($n_s$) of the brewed coffee sample and a quadratic function of the temperature of the brewed coffee sample. In another embodiment, the TDS formula expresses TDS as a quadratic function of index of refraction ($n_s$) of the brewed coffee sample and a quadratic function of the temperature of the brewed coffee sample.

BRIEF DESCRIPTION OF THE DRAWINGS

The appended drawings illustrate only exemplary embodiments of the invention and therefore do not limit its scope, because the inventive concepts lend themselves to other equally effective embodiments.

FIG. 4B shows a conventional brewing chart for grams coffee per liter of water.

FIG. 4C shows a conventional brewing chart for ounces coffee per 1.0 gallon water.

FIG. 4D shows a conventional brewing chart for ounces coffee per half gallon water.

FIG. 4E shows a conventional brewing chart for ounces coffee per 1.0 quart water.

FIGS. 7A-7B show a representative coffee design and measurement process flow.

FIG. 9D is a flowchart that depicts process flow in a ground coffee weight mode of the disclosed methodology.

FIG. 10A is a block diagram of the disclosed coffee refractometer.

FIG. 10B is a block diagram of a brewing station that employs the disclosed coffee design system and the disclosed coffee refractometer.

FIG. 11A is a flowchart that depicts process steps in calibrating and correlating the disclosed refractometer to read total dissolved solids (TDS).

DETAILED DESCRIPTION

Figure 1:
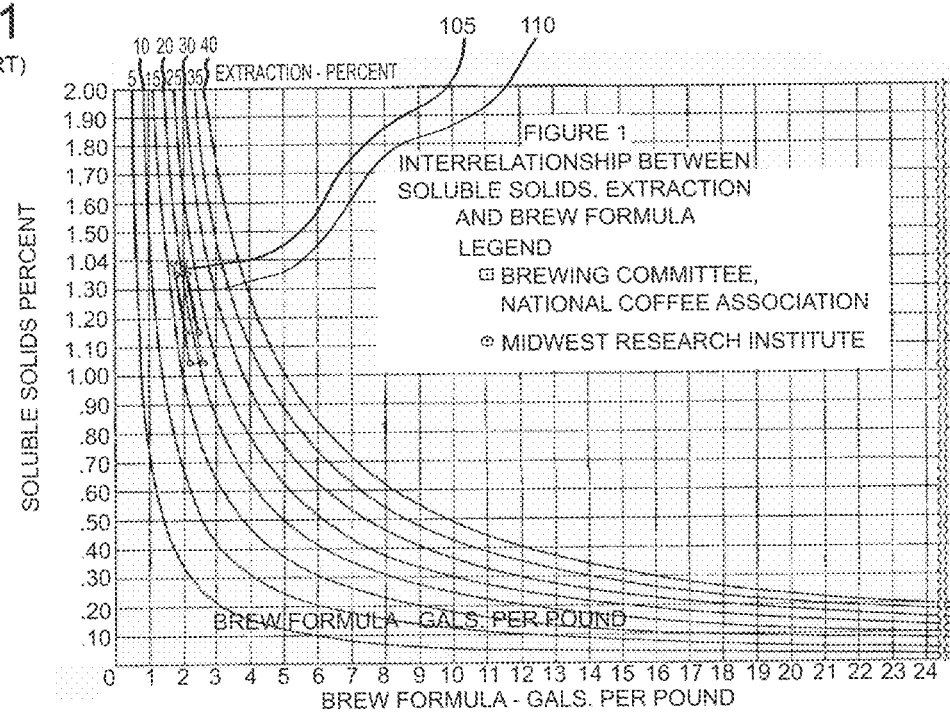
FIG. 1 shows a conventional soluble solids, extraction and brew formula graph.
Figure 2:
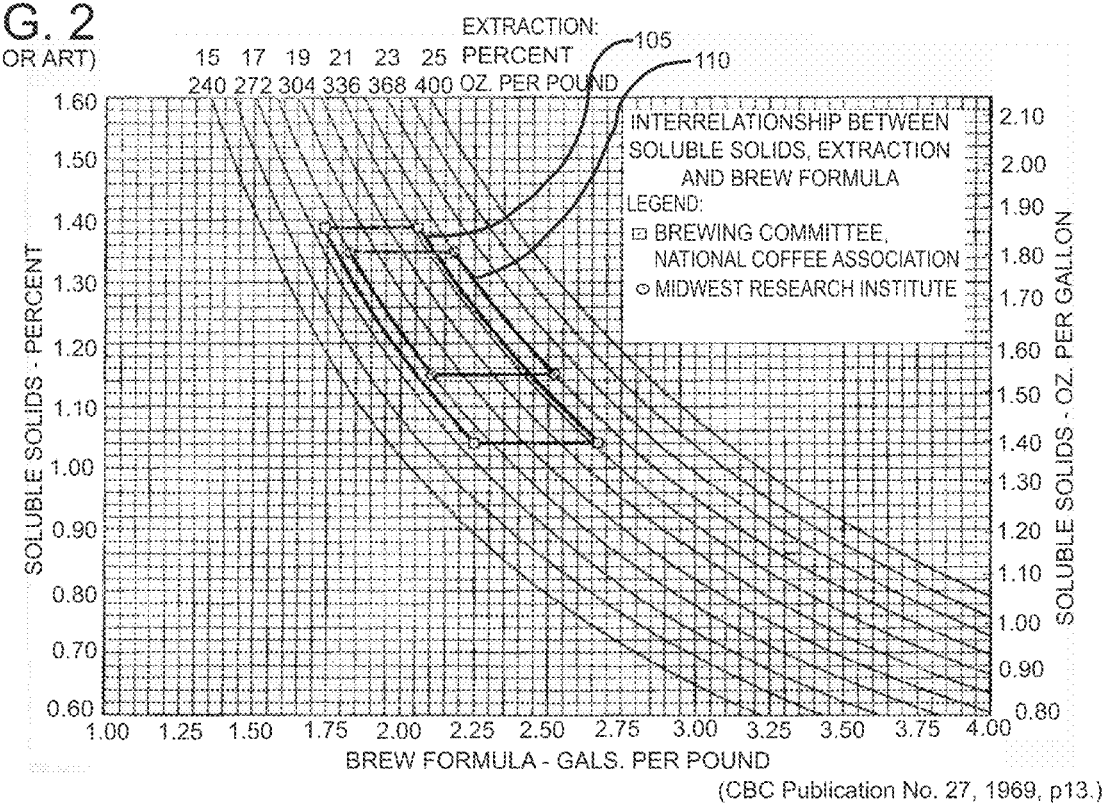
FIG. 2 shows an expanded view of a conventional soluble solids, extraction and brew formula graph with specific regions of interest.

FIG. 1 is a prior original brewing chart that shows soluble solids vs. brew formula as a function of extraction percent, namely 5-40 percent as seen in the upper left of the chart (CBC Publication No. 27, 1969, p12.). The y axis represents soluble solids concentration (strength) in percent while the x axis represents the brew formula in gallons of water per pound of coffee. Hyperbolic curves representing soluble solids yield extraction in percent from 5-40% are illustrated. Of particular interest in this series of hyperbolas are region of interest 105 and the smaller region of interest 110. Region of interest 105 relates to a study carried out by the Brewing Committee of the National Coffee Association, which judged brews prepared within this region for objective acceptability. The Midwest Research Institute carried out a more recent independent study from which it was concluded that the most acceptable coffee would result from preparation within the more refined region of interest 110, for soluble solids concentration (strength) from 1.15 to 1.35 percent and soluble solids yield extraction between 18 and 22 percent (Niven, W. W., Jr. and Shaw, B. C., Critical Conditions for Quality Coffee Brewing, Coffee and Tea Industries 80, No. 4, 44, April. 1957. Tea and Coffee Trade Journal, 112, No. 4, 28-April. 1957. Coffee Brewing Center, Nos. 19 and 27, 1969. The brewing chart of FIG. 1 signifies that a very small area of the curves thereof (i.e. region of interest 105 or region of interest 110) should be targeted for proper coffee extraction relative to the wide range of extraction possible. FIG. 2 is an enlargement of a portion of the brewing chart of FIG. 1 focusing on regions of interest 105 and 110.

Figure 3:
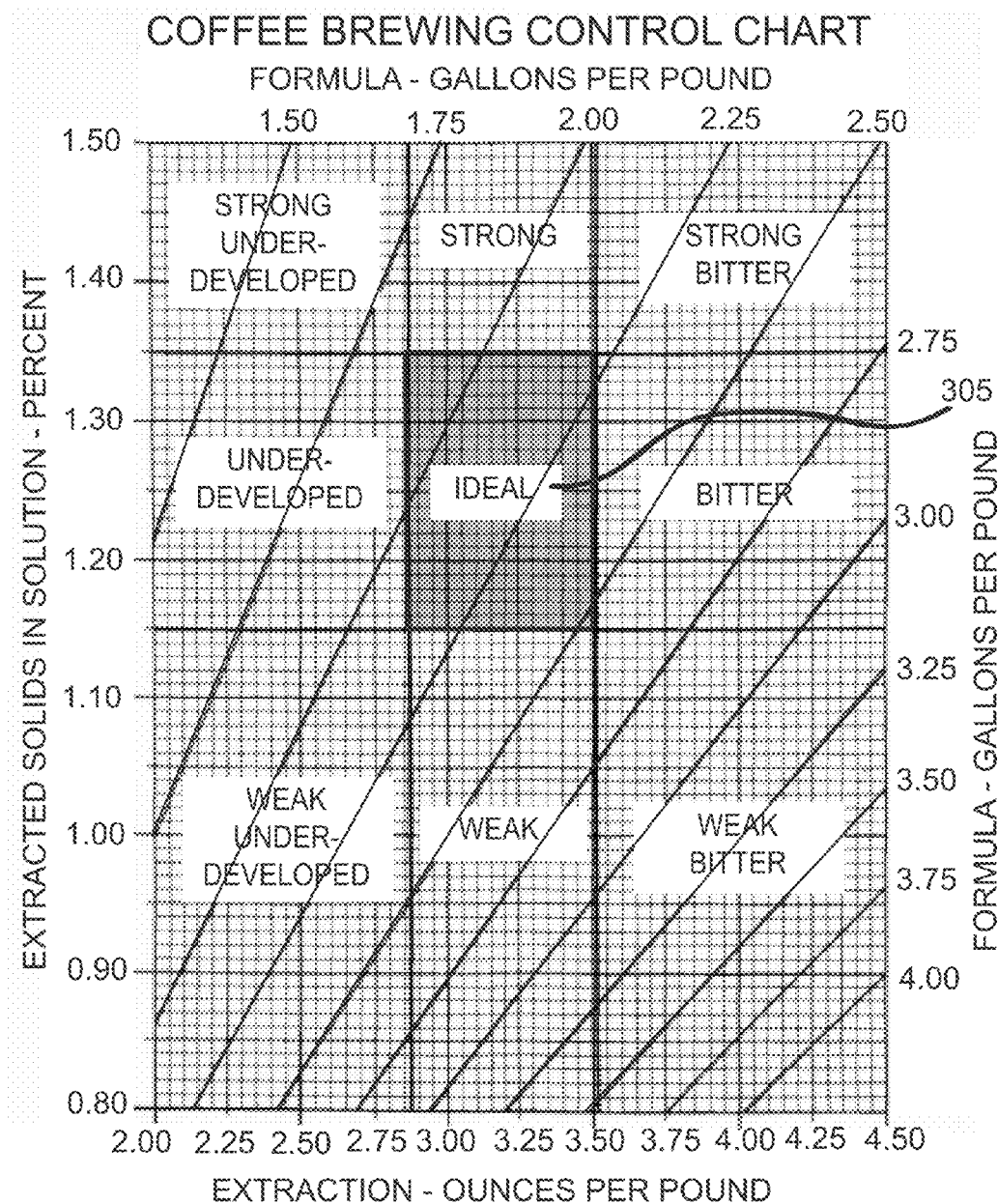
FIG. 3 shows a conventional soluble solids, extraction and brew formula chart with soluble solids represented in percent.

FIG. 3 is a conventional representation of the data for FIG. 1 and FIG. 2 including solubles concentration (strength) vs. solubles yield (extraction) with brew formula as the parameter. More particularly, the y axis of FIG. 3 represents extracted solids in solution (percent TDS or total dissolved solids) while the x axis represents extraction in ounces per pound (solubles yield). The plotted curves are nearly straight lines (curves) that correspond to the brew formula in gallons of water per pound of coffee. The plot of FIG. 3 identifies a substantially centered rectangular region of interest 305 as representing the ideal coffee brew. This region of interest 305 is the same as originally published by the CBC and as identified as developed by the Midwest Research Institute, region 110, previously in FIGS. 1 and 2. These plots assume the specific gravity of water at ambient temperature which may in fact be substantially different from the specific gravity of water at the actual brewing temperature. This assumption may have a negative impact on the brewing process and may affect the ability to reach a particular target percent of TDS of coffee in solution and a particular percent extraction if the ratio of coffee to water is determined at an incorrect temperature. Since the density of water changes as a function of temperature, the volume of water to weight of coffee ratios are affected accordingly. To further illustrate this problem, commercial brewer-extractors are typically preset to approximately 200 degrees F. and volume is calibrated at the boiler set point, whereas a home brewer typically uses water at tap or room temperature, i.e. an ambient temperature of approximately 50-65 degrees F. The volume of a given weight of water at room temperature will be significantly less than the volume of the same weight of water at 200 degrees F., because water is more dense at ambient than at 200 degrees. This scenario can lead to inaccurate brewing results when using the coffee brewing chart of FIG. 3.

Figure 4A:
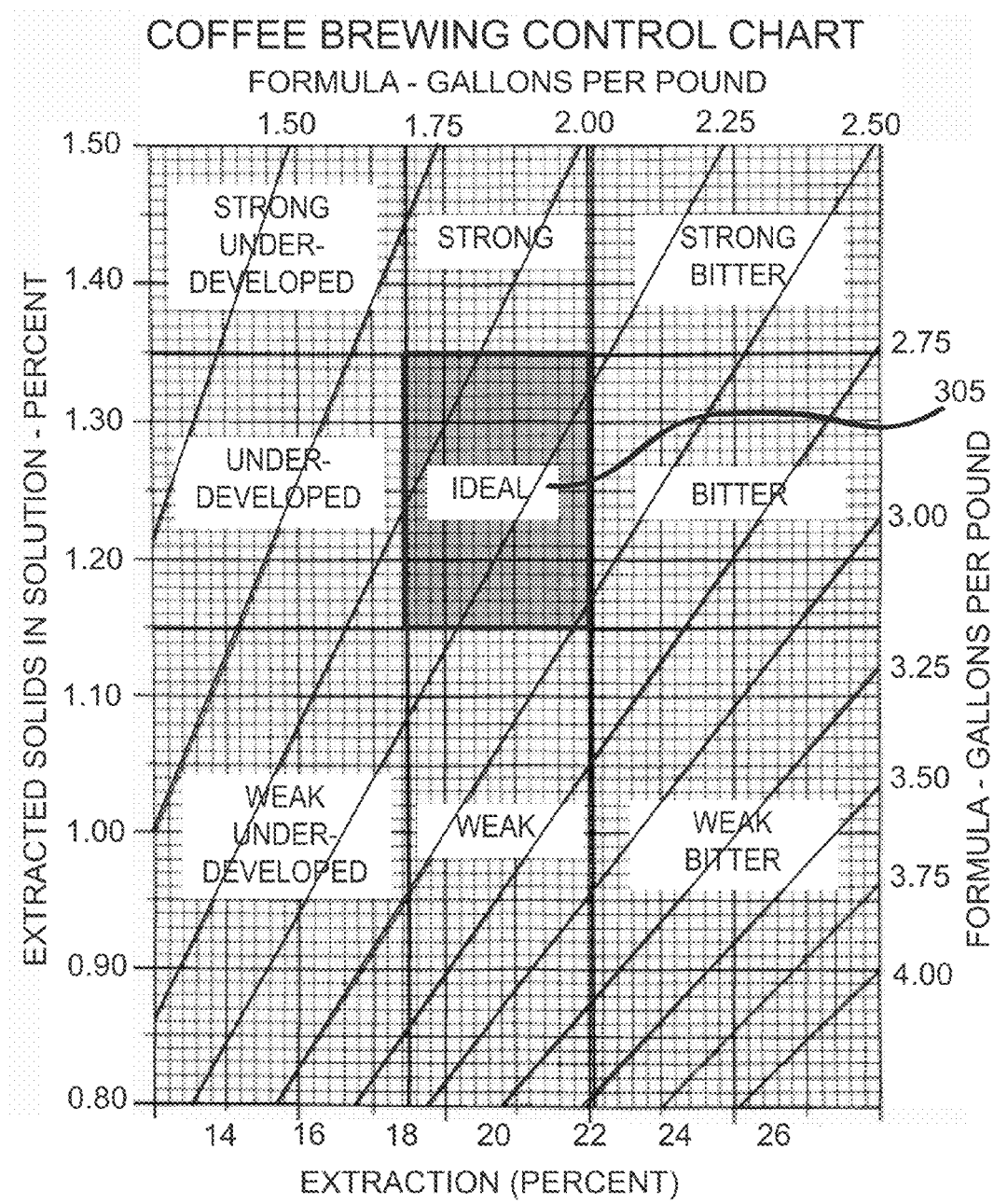
FIG. 4A shows the conventional soluble solids, extraction and brew formula chart of FIG. 3 with both soluble solids and extraction represented in percent.

FIG. 4A is substantially the same coffee control brewing chart of FIG. 3 except that the x axis is now expressed in percent extraction, a more convenient unitless method of expression, instead of ounces extracted per pound of coffee. For example, if 3.2 ounces of coffee are extracted from 16 ounces of coffee, this corresponds to 20% extraction by weight. While the parameters of the x axis and y axis are expressed in percent, the brew formula of FIG. 4A remains in units of gallons of water per pound of coffee, as was the case in the brewing chart of FIG. 3. FIGS. 4B-4E show a similar conventional representation of the typical brewing chart in common use today. For each brew batch size and unit of measure, separate conventional representations are needed, where such representations show separate brew formulas each labelled for the weight of ground coffee called for in that dedicated batch size. FIGS. 4B-4E show separate charts required for each separate batch size, and units of measure used, including gallons of brew water per ounce of ground coffee, similarly half-gallons per ounce, liters per gram and quarts per ounce. Expressed alternatively, FIG. 4B is a conventional brewing chart for grams coffee per liter water. FIG. 4C is a conventional brewing chart for ounces coffee per 1.0 gallon water. FIG. 4D is a conventional brewing chart for ounces coffee per half gallon water. FIG. 4E is a conventional brewing chart for ounces coffee per 1.0 quart water.

Figure 5:
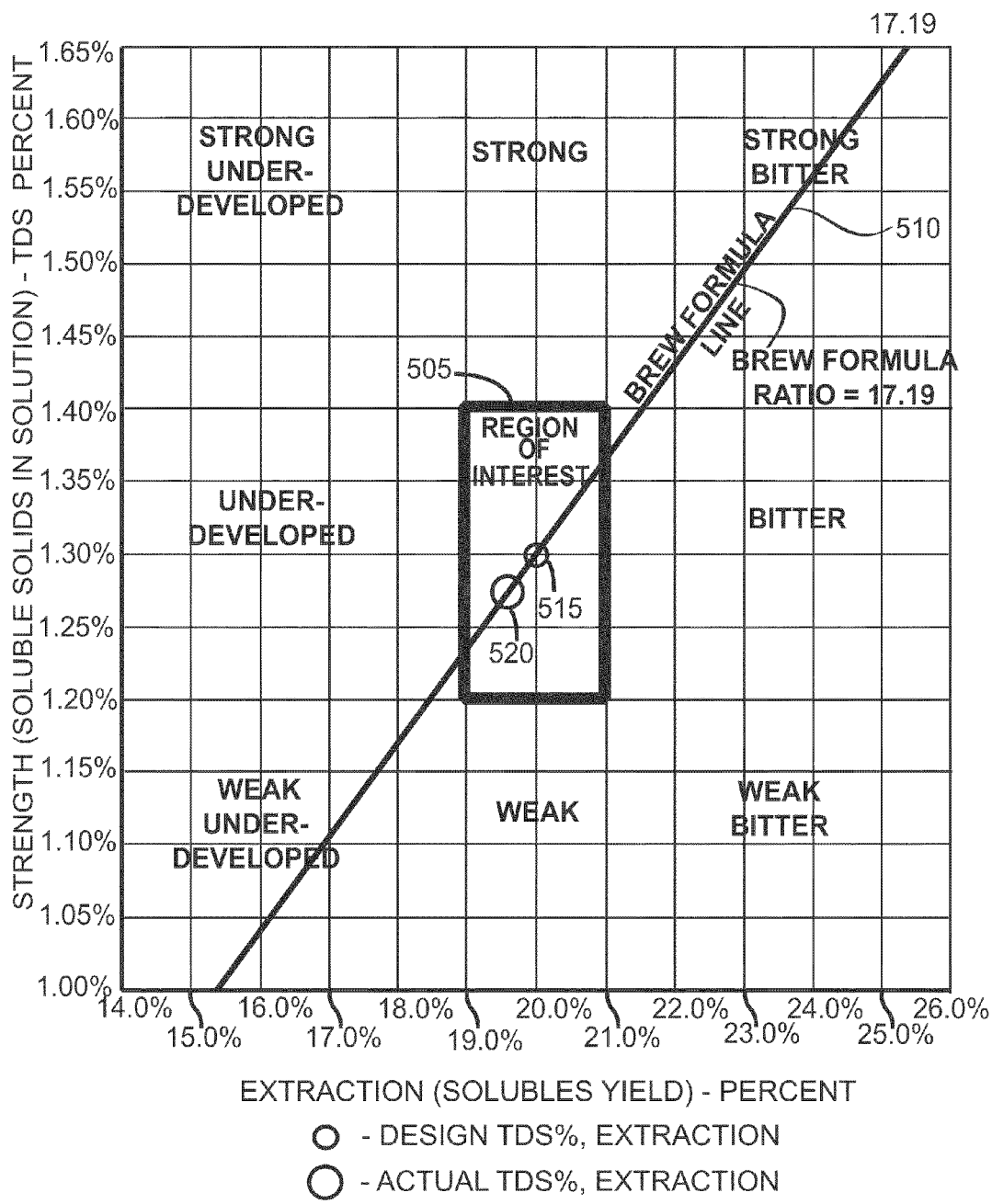
FIG. 5 shows one embodiment of the disclosed universal coffee brewing chart with a particular representative brew formula line that extends through a region of interest that includes both a target coffee design point and an actual coffee design point.

FIG. 5 shows the universal coffee brewing chart that the disclosed coffee design software application may generate. Rectangle 505 denotes a region of interest of acceptable strength in percent total dissolved solids (% TDS or solubles concentration) and extraction percent (solubles yield) that are found to be very desirable for the experienced palate, typically from approx. 1.2% to approx. 1.4% strength and approx. 19% to approx. 21% extraction, more typically from approx. 1.15% to approx. 1.55% strength and approx. 18% to approx. 22% extraction. Such regions of interest may be defined specifically as being best suited for particular coffee cultivars, regions, roast styles, and terroir, and may be developed specifically as preferences or suggested recipes for brewing particular coffees, and may be further developed as a result of consumer taste profiles and overlaid as new regions of interest to suit a particular consumer preference, roaster preference or user preference. For example, consumer preferences may be plotted on an additional z-scale, and consider an n-point scale (from "like intensely" to "dislike intensely") which is plotted as a three-dimensional surface chart, where the y-scale is solubles concentration (%) and the X-scale is solubles yield (%). The surface chart may then be resolved to a colorized two-dimensional chart by viewing the three-dimensional chart from the top, and plotting the z-axis (consumer preference) in colors and in two dimensions, along with the traditional solubles yield (percent extraction) and solubles concentration (percent TDS, strength) superimposed on the same two-dimensional chart. Such a representation may provide an update to the most recent "optimum balance" regions of interest, and as corrected for brew water temperature.

Brew formula line 510 represents the brew formula of water and coffee and makes the brew formula a dimensionless unit of measure by stating brew formula as a ratio (e.g. 17.19) of water to coffee by weight. This ratio remains constant despite variations in size of coffee batches brewed or the units used, thereby eliminating a requisite of separate brewing control charts for each different unit of measure or changes in batch size, as required in the past with conventional brewing control charts. Unfortunately, the conventional brewing control charts of FIGS. 1-3, 4A-4E are not flexible because a different brewing control chart is needed each time brewing batch size or units of measure changes. Moreover in these conventional charts, mixed units of volume of water are used with weight measurement units of coffee, mandating a new chart whenever a unit of measure or batch size changed. However, in one embodiment, the disclosed coffee design application and system is capable of generating a universal coffee brewing control chart that is stepless in portion sizes and continuous as coffee batch size, brew formulas, extraction and strength changes and as other variables change. The universal coffee brewing control chart also manages variable and mixed units, for example, brew water may be specified in gallons and coffee weight in grams, or water in liters and coffee weight in ounces. The disclosed coffee design application converts water volume at the temperature specified to weight to plot the correct brew formula ratio. Previous original brewing charts assumed water at room temperature, and conventional charts assumed water at 140 degrees F. as corrected for the hydrometer instrument used. However, the disclosed coffee design application corrects for the actual brew water temperature. The disclosed coffee design application will replot the control chart steplessly and in real time as the user changes design inputs. For example, as brew strength increases, brew formula line 505 may be continuously replotted to the left and higher in FIG. 5. Likewise, as brew strength decreases, brew formula line 505 may shift continuously to the right and lower in FIG. 5. With each change in the brew formula line, all other design output parameters are calculated and displayed continuously and in real time, and portions are determined based on actual start and brew water temperatures to maintain portions true to the brew formula ratio, eliminating previous errors in the range of 2-4%. With the universal coffee brew control chart that this application provides, there is no need for a series of different brew control charts for each batch size or units of measure.

The following EQUATION 1 determines Percent Extraction using the Brew Formula Ratio, Water Density at Brew Temp and Percent TDS as variables. More particularly, from TDS %=0 to TDS %=10, the disclosed coffee design application determines Extraction for each TDS point using EQUATION 1:

$$\text{EXTRACTION \%} = (BF \text{ Ratio} - \text{water density\_(g/ml @ brew Temp)} * \text{waterLost\_ml/g\_coffee})/(1/TDS\%-0.01)) \quad \text{Equation 1}$$

To calculate Extraction % using this equation, Brew Formula Ratio (BF Ratio) should first be determined from the user input using the Strength Slider (TDS %) setting and the Target Extraction %. If the user changes the Strength Slider, then the BF Ratio changes and the brew formula line moves to a new location on the brew chart. Water density at brew temperature and water lost per gram are constants. Equation 1 is not a linear equation. The disclosed coffee design application plots the resulting point pairs on the control chart of FIG. 5 to draw the brew formula line 510.

The brew formula line 510 is drawn from generated data point pairs by incrementing Percent TDS from 0 to 10 and calculating Percent Extraction. The universal coffee brewing chart of FIG. 5 plots Percent TDS vs. Percent Extraction. The slope of the brew formula line 510 is delta TDS over delta Extraction, namely change in TDS over change in extraction. The Brew Formula is used to calculate these point pairs. As will be explained in more detail below, the disclosed coffee design application will plot the intended coffee design as a small circle 515 (red plot point) for strength (solubles concentration) and extraction (solubles yield) on the brew formula line 510. Subsequently, after brewing a sample batch of coffee according to the specified design parameters and measuring the total dissolved (TDS %) with the disclosed coffee refractometer, the disclosed coffee application will plot the actual measured coffee design as a large circle 520 (blue plot point) for strength (solubles concentration) and extraction (solubles yield) on the brew formula line 510.

Figure 6A:
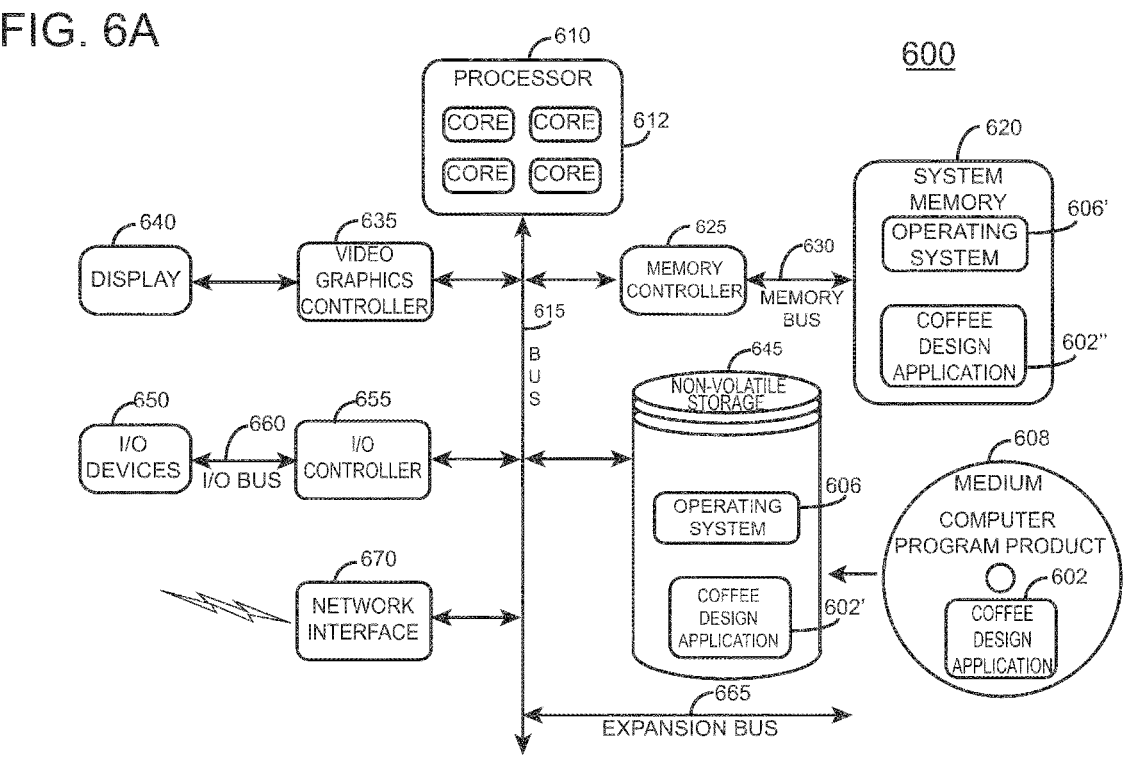
FIG. 6A shows an information handling system (IHS) including the disclosed coffee design application embodied in a computer program product.

FIG. 6A shows an information handling system 600 on which the coffee design application may execute as a computer program product. More particularly, FIG. 6 shows an information handling system (IHS) 600 that includes coffee design application 602 and an operating system 606. IHS 600 may initially store coffee design application 602 as a computer program product on a medium 608, such as a CD, DVD or other medium. In this particular embodiment, IHS 600 includes a processor 610 having multiple compute elements (CEs) on a common semiconductor die 612. IHS 600 processes, transfers, communicates, modifies, stores or otherwise handles information in digital form, analog form or other form. IHS 600 includes a bus 615 that couples processor 610 to system memory 620 via a memory controller 625 and memory bus 630. A video graphics controller 635 couples display 640 to bus 615. Nonvolatile storage 645, such as a hard disk drive, CD drive, DVD drive, or other nonvolatile storage couples to bus 615 to provide IHS 600 with permanent storage of information. Operating system 606 loads in memory 620 to govern the operation of IHS 600. I/O devices 650, such as a keyboard and a mouse pointing device, couple to bus 615 via I/O controller 655 and I/O bus 660. One or more expansion busses 665, such as USB, IEEE 1394 bus, ATA, SATA, PCI, PCIE and other busses, couple to bus 615 to facilitate the connection of peripherals and devices to IHS 600. A network interface adapter 670 couples to bus 615 to enable IHS 600 to connect by wire or wirelessly to a network and other information handling systems. While FIG. 6A shows one IHS that employs processor 610, the IHS may take many forms. For example, IHS 600 may take the form of a desktop, server, portable, laptop, notebook, or other form factor computer or data processing system. IHS 600 may take other form factors such as a gaming device, a personal digital assistant (PDA), a handheld computing device, a portable telephone device, a communication device or other devices that include a processor and memory.

A user of IHS 600 loads medium 608 into IHS 600 to store coffee design application 602 on non-volatile storage 645 as coffee design application 602'. When IHS 600 initializes, the IHS loads operating system 606 into system memory 620 for execution as operating system 606'. The IHS also loads coffee design application 602' into system memory 620 for execution as coffee design application 602".

Figure 6B:
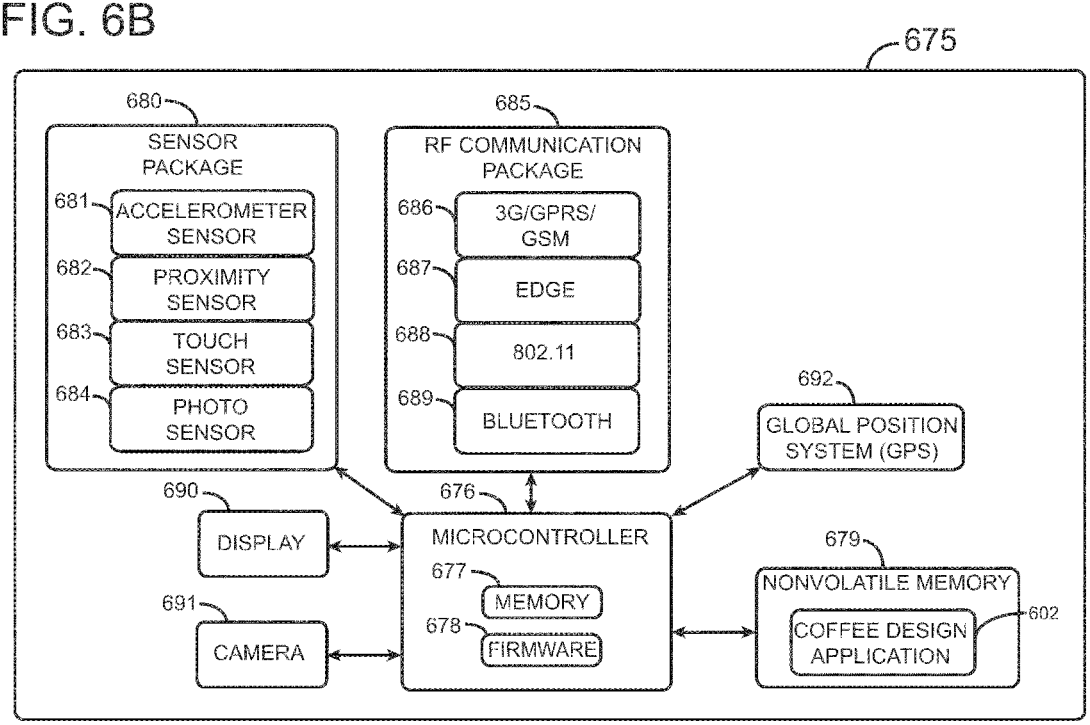
FIG. 6B shows a small form factor handheld information handling system (IHS) including the disclosed coffee design application embedded or stored therein.

FIG. 6B shows a hand-held information handling system 675 that exhibits a small form factor such as a personal digital assistant (PDA). For example, IHS 675 may be a portable telephone type device or hand-held computer, such as an IHS that executes Microsoft Windows CE, or a Palm Pilot type device or an iPhone type IHS or smart phone. (PalmPilot is a trademark of Palm, Inc. iPhone is a trademark of Apple Inc.) In this embodiment, coffee design application 602 is embedded within the small form factor IHS as shown in FIG. 6B. In more detail, hand-held IHS 675 includes a microcontroller 676 that includes an internal memory 677 and firmware 678. IHS 675 includes a non-volatile memory 679 coupled to microcontroller 676. In one embodiment, non-volatile memory 679 stores coffee design application 602 therein as shown. In another embodiment, firmware 678 may contain coffee design application 602 or memory 677 may contain coffee design application 602.

IHS 675 includes a sensor package 680 that includes an accelerometer sensor 681, a proximity sensor 682, a touch sensor 683 and a photo sensor 684. Sensor package 680 couples to microcontroller 676. IHS 675 further includes an RF communication package 685 that includes a 3G/GPRS/GSM phone communication module 686, and EDGE phone communication module 687, an IEEE 802.11 network communication module 688 and a Bluetooth local communication module 689. RF communication package 686 couples to microcontroller 676. Both a touch sensitive display 690 and a camera 691 couple to microcontroller 676 as shown. A global positioning system (GPS) module 692 also couples to microcontroller 676 to provide position information thereto.

In one embodiment, sensor package 680 generates a first position signal when IHS 675 exhibits a first spatial position or orientation such as a horizontal position, for example, with respect to a particular reference point. Sensor package 680 generates a second position signal when IHS 675 exhibits a second spatial position or orientation such as a vertical position with respect to the particular reference point. IHS 675 is configured to send the first and second position signals to coffee design application 602. IHS 675 is further configured such that coffee design application receives user input from touch screen display 690 when sensor package 680 generates the first position signal indicating that the IHS 675 is in the first position. Coffee design application 602 responds to the first position signal and accepts user input when it receives the first position signal. For example, such user input may include user input preferences to set modes and temperatures, and user input commands to accept % TDS strength and other input variables using a combination of touch screen commands, buttons and text or number entry modes.

When coffee design application 602 receives the second position signal, indicating that the user has changed the orientation of the IHS 675 to the second position, coffee design application 602 senses this signal change and in response computes and plots the solution and charts results of the user inputs, including but not limited to the brew formula curve, required portions of coffee and water, and draws a universal brewing control chart on display 690. In other words, the user holds IHS 676 horizontally while inputting information and flips the IHS 675 to a vertical position to command that IHS 675 draw a universal brewing control chart on the display 690. It is noted that the first and second positions are described as being horizontal and vertical, respectively, for purposes of example. The disclosed IHS applies as well to other first and second positions or spatial orientations without departing from the spirit of the invention.

Figure 7A:
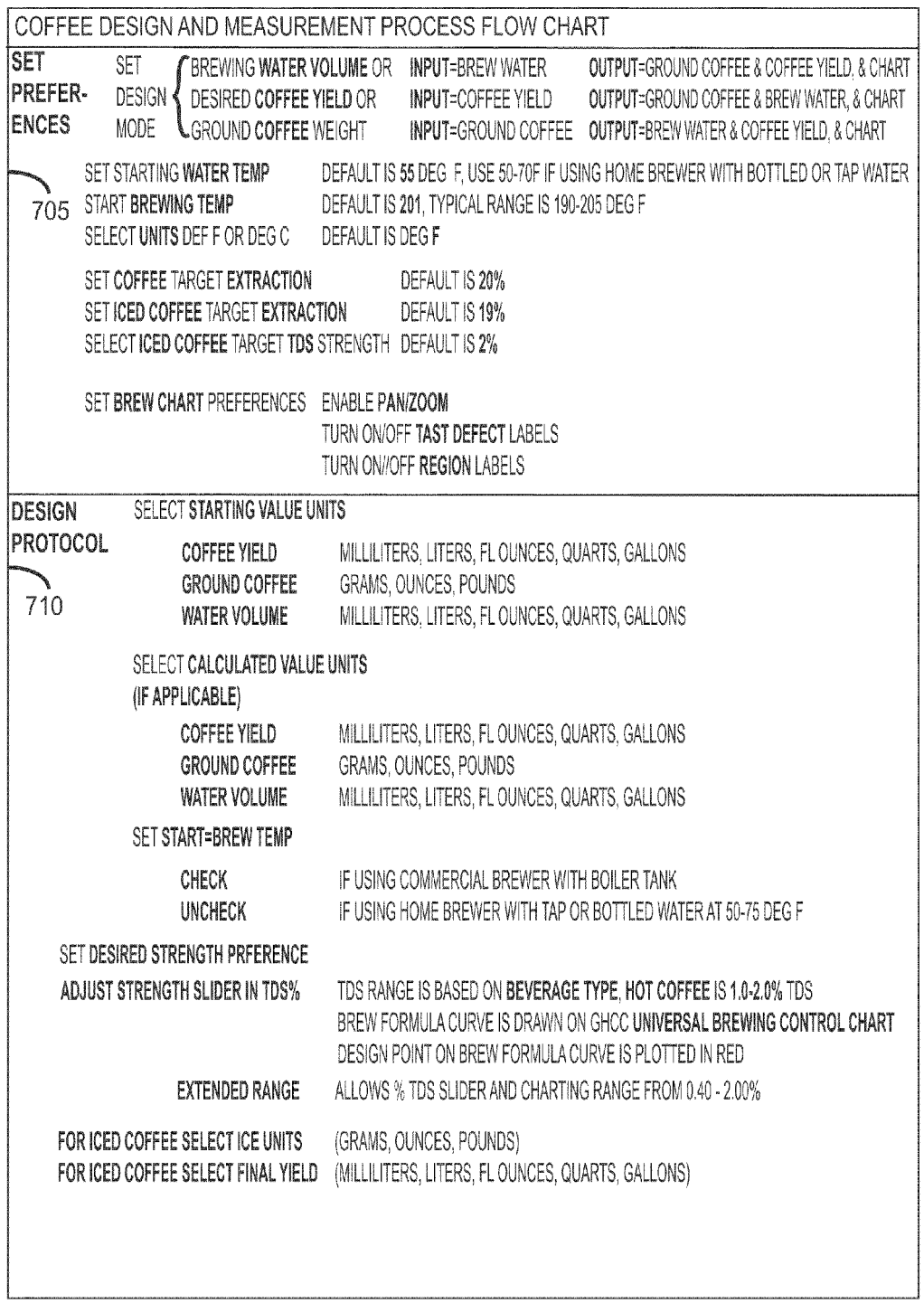

FIGS. 7A-7B show depicts a textual representation of the disclosed coffee design process including 1) setting user preferences at set preferences block 705, 2) conducting the design protocol at design protocol block 710, 3) performing a total dissolved solids (TDS) measurement with a refractometer at TDS measurement block 715, 4) correcting the brew protocol if necessary (included in block 715), 4) saving data at block 720, and 5) printing data at block 725. The process also includes providing help information at block 730. The processor further includes an "about the program" block 730 with design credits, legal notices and license key information.

FIGS. 7A-7B show provides a high level overview of the coffee design process. The screen shots of FIG. 8A-8J will provide more detail with respect to the coffee design process and are discussed below following discussion of the FIGS. 7A-7B high level process. The user sets preferences in set preferences block 705. More particularly, the user may select one of three different coffee design modes as a starting preference, namely: Start By Entering 1) brewing water volume 2) desired coffee yield or 3) ground coffee weight. In brewing water volume design mode, the user inputs starting brewing water volume and the desired strength (solubles concentration) % TDS as input values. In response, coffee design application 602 determines or computes the brew formula, and determines the remaining two variables, namely ground coffee weight and resulting coffee yield volume. In desired coffee yield mode, the user inputs the desired coffee yield in volume and the desired strength (solubles concentration) % TDS. In response, coffee design application 602 computes the brew formula, and determines the remaining two variables, namely the required brew water volume and ground coffee weight. In ground coffee weight mode, the user inputs the ground coffee weight and the desired strength (solubles concentration) % TDS. In response, coffee design application 602 computes the brew formula, and determines the remaining two variables, namely the required brew water volume and resulting coffee yield volume.

In set starting preferences block 705, the user may select the starting water temperature. In one embodiment, the default starting water temperature is 55 degrees F. However, a user may select a starting water temperature between 55 and 70 degrees F. if the user is using a home brewer with bottled or tap water. The user may also select a brewing temperature in block 705. The default brewing temperature is 201 degrees F. in one embodiment. The user may select a brewing temperature that is typically between 190 and 205 degrees F. The user may also specify temperature units in degrees F. or degrees C. in block 705.

In set starting preferences block 705, the user may also select target settings for the coffee brewing process. For example, the user may input a coffee target extraction (solubles yield). The default coffee target coffee extraction is 20%, but for some coffees, a user may want to target a lower value, such as 19.5%, to emphasize sweetness, or sugars content, typical of high elevation grown coffees, for example. For other coffees that lack certain types of acidic components, one may want to select a higher target extraction, such as 22%, for example, since higher solubles yield (extraction) of that particular coffee will not extract bitter components. The user may also specify an iced coffee target extraction for which the default is 19%, to emphasize sweetness. The user may also specify a finished iced coffee target TDS strength for which the default is 2% after dilution and brewing over ice. The user may also specify and input brew chart preferences such as enabling pan and zoom on the universal brewing chart (discussed below), turning on and off taste defect labels and turning on and off region labels, as well as specifying custom regions of interest by particular coffees and or consumer preference regions. In a special case, ICED Coffee final strength target is set by the user as a preference to provide the coffee design application an input for calculation of 97% ice melt (and dilution) of concentrate which starts at a concentration strength TDS of 3.8%, and ending up at 2.0% after dilution (ICE melt).

In the design protocol block 710 of the process flow of FIGS. 7A-7B, the user may select or input desired starting value units. For example, for coffee yield the user may specify volume units such as milliliters, liters, fluid ounces, quarts or gallons. In another embodiment, coffee yield units may be selected as weights, rather than volume, for example, grams, kilograms, ounces or pounds. For ground coffee weight, the user may specify one of grams, kilograms, ounces or pounds. For water volume, the user may specify as milliliters, liters, fluid ounces, quarts or gallons. In an other embodiment, brew water units may be selected as weights, rather than volume, for example, grams, kilograms, ounces or pounds. In the design protocol block 710, the user may then enter input value in the units selected in the previous step, as well as the desired strength in percent TDS. For example, in the case of coffee yield in volume, the user may specify the desired coffee yield as 2 liters, or 1.5 gallons. For ground coffee weight, the user may specify one of grams, kilograms, ounces or pounds. For water volume, the user may specify as milliliters, liters, fluid ounces, quarts or gallons. In each mode, the % TDS is also selected as in an input value. For coffee brewing protocols, brew water and coffee yield are typically measured in volume for practical reasons, due to the ease of measurement of such bulk in volume versus weight, as long as temperature (and density) are taken into account. However, in espresso, or single-serve coffee, where volumes are typically much smaller, for example, for a single-serve portion, measurements are more practical and also more accurate when specified in weight.

In the design protocol block 710, the user may also input a selection that the start temperature is the brew temperature if desired. More particularly, the user may select a "start temperature=brew temperature" checkbox (discussed below in FIG. 8) by checking such box if using a commercial brewer with a boiler tank or may leave the checkbox unchecked if using a home brewer with tap or bottled at 50-75 degrees F. The user may also select the desired strength preference within design protocol block 710. The user may adjust and select the desired strength preference by moving an adjust strength slider (discussed below in FIG. 8). The adjustable strength slider selects desired strength in total dissolved solids (TDS) percent.

The TDS range accessible by the strength slider is based on beverage type. For hot coffee, the selectable range varies from 1.0-2.0% in one embodiment. The user may select an extended strength range, such as a range between 0.40 and 2.00% in one embodiment by checking an "Extended Range" checkbox in set preferences block 705 (discussed below in FIG. 8). Alternatively, the user may select an extended strength range, such as a range between 0.40 and 3.60% in one embodiment by checking an "Extended Range 2" checkbox in set preferences block 705 (discussed below in FIG. 8). Extended ranges are useful for troubleshooting existing coffee brewing protocols in the field that are being evaluated to be corrected, and may not be within normal ranges, due to significant brew formula portioning errors in excess of 5-8%, for example, or excessive extraction errors, for example. In another embodiment, the user may select any extended strength range, such as a range between 3.0% and 4%, to cover a range more appropriate for coffee concentrates, such as for iced coffee, or for hot coffee to be diluted to a desired strength preference by addition of hot water to the brewed concentrate, for a single serve beverage brewer, for example. In another embodiment, the user may select any extended strength range, such as a range between 3.0% and 18%, to cover a range more appropriate for espresso, for example.

Upon selection of the desired strength preference and the other input values and selection of units, coffee design application 602 generates a brew formula curve or line which is plotted on a universal coffee brewing chart such as shown in FIG. 5. Recall that the universal coffee brewing chart of FIG. 5 plots Percent TDS vs. Percent Extraction. The slope of the brew formula line 510 is delta TDS over delta Extraction. The Brew Formula Ratio is used to calculate point pairs using Equation 1. The plotted brew formula line takes into account the volume of water as a function of temperature, and computes the correct weight of coffee required to meet the specified brewing protocol, and the resulting finished coffee yield.

The target strength selected is plotted on the brew formula line as a small circle 515 (red point) and represents the targeted design parameters. The user then proceeds to brew the coffee using the design output parameters that coffee design application 602 generates. If the user selected brew water volume and % TDS as input conditions, coffee design application 602 then determines the resulting coffee yield volume and required ground coffee weight values corresponding to those input conditions. If the user selected desired coffee yield volume and % TDS as input conditions, coffee design application 602 then determines the required brew water volume and ground coffee weight values corresponding to that input condition. If the user selected coffee weight and % TDS as input conditions, coffee design application 602 then determines the required brew water volume and resulting coffee yield volume corresponding to those input conditions. The user then employs the particular input conditions and corresponding values to actually brew a test batch of coffee.

As part of the coffee design process of FIGS. 7A-7B, the user brews a sample of the targeted design batch of coffee as specified by the input conditions and corresponding determined variable values or results. The user places a sample of the test batch into the disclosed coffee refractometer (see FIG. 10 below) to determine the total dissolved solids (TDS) % by measuring the index of refraction of the brewed coffee sample. Before using the refractometer, the user first calibrates the refractometer using distilled water. The refractometer and water should preferably be within the temperature range of 20 degrees-25 degrees C., in one embodiment. The user cools a 10-20 ml sample of the brewed coffee to between 20 degrees C. and 30 degrees C. The user places the cooled sample into the refractometer and allows 1-2 minutes for the sample and the refractometer to reach the same temperature.

After temperature stabilization, the user takes a TDS % reading, as per bock 715. The user then enters the TDS reading into coffee design application 602. In response, coffee design application 602 adds a large circle plot point 520 (blue point) on the same brew formula line 510 of the universal coffee brewing chart of FIG. 5 generated during the design step. The large circle (blue point) % TDS measurement shows where the current coffee batch falls on that chart relative to the intended design point 515 (small red plot point) for strength (solubles concentration) and extraction (solubles yield). After observing where the current coffee batch results appear on the universal coffee brewing chart, the user may take corrective action, if necessary, to ensure that the final coffee design for subsequent batches of coffee falls within the parameters of the desired region of interest. Such corrective action may include:

1) Under-Extraction: If the blue large circle plot point 520 (blue point) is outside of the desired region of interest, below and to the left on the brew formula line 510, the batch was under-extracted, and likely exhibits a taste defect associated with under-developed flavors. Common causes of under-extraction are too coarse a grind, too short a contact time with water during the brew period, lack of pre-infusion or pre-infusion levels too low and/or time too short, water too hard (mineral content too high), brew temperature too low, and/or lack of even wetting or turbulence in the brew basket.

2) Over-Extraction: If the large circle plot point 520 (blue point) is outside of the desired region of interest, above and to the right on the brew formula line 510, the batch was over-extracted, and likely exhibits a taste defect associated with over-extracted bitter flavors. Common causes of over-extraction are too fine a grind, too long a contact time with water during the brew period, pre-infusion levels too high and/or time too long, too much turbulence in the brew basket, water too soft (too low a mineral content), and/or brew temperature too high.

Figure 8A:
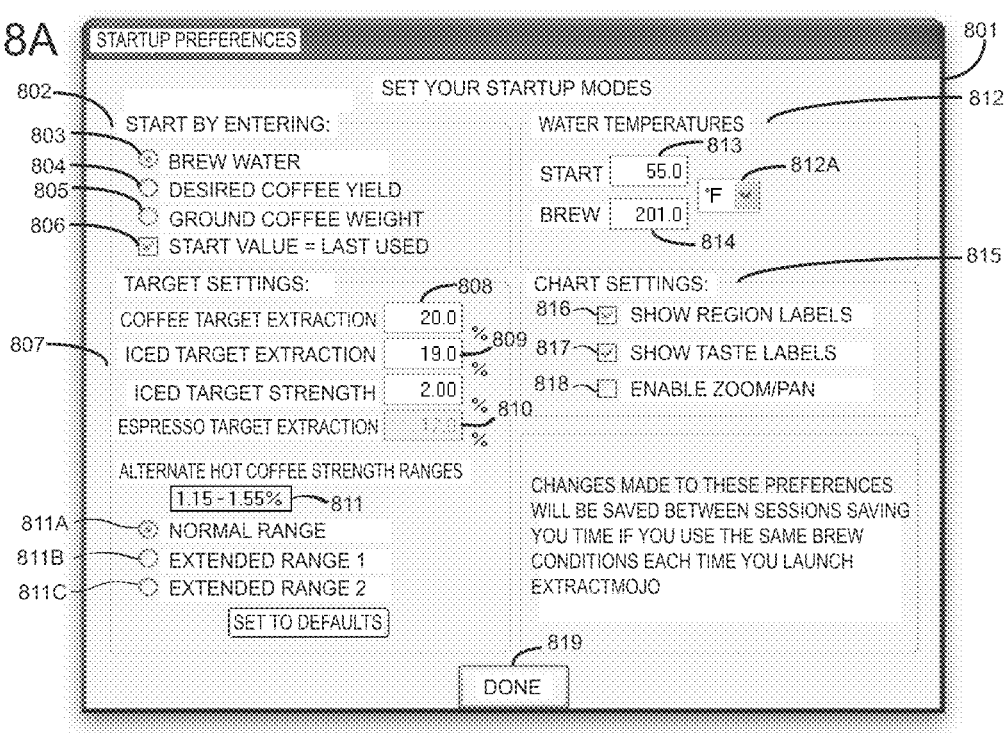
FIG. 8A shows a startup preferences window of the disclosed coffee design application wherein a brew water volume mode is selected.
Figure 8B:
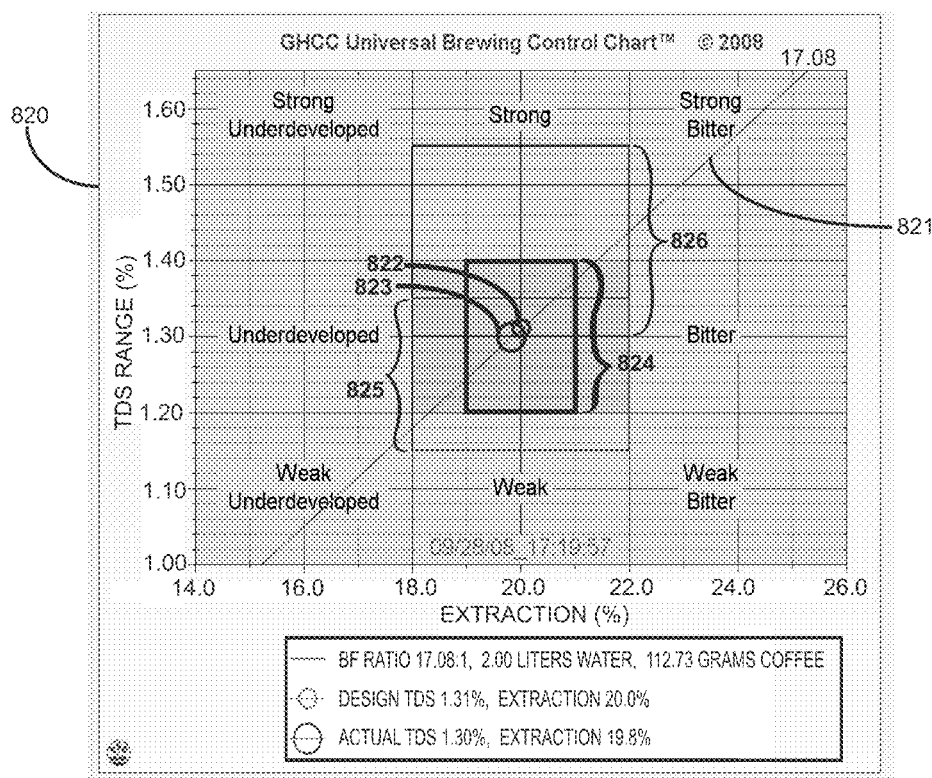
FIG. 8B shows a universal brewing control chart resulting from the disclosed coffee design application operating in the brew water volume mode.
Figure 8C:
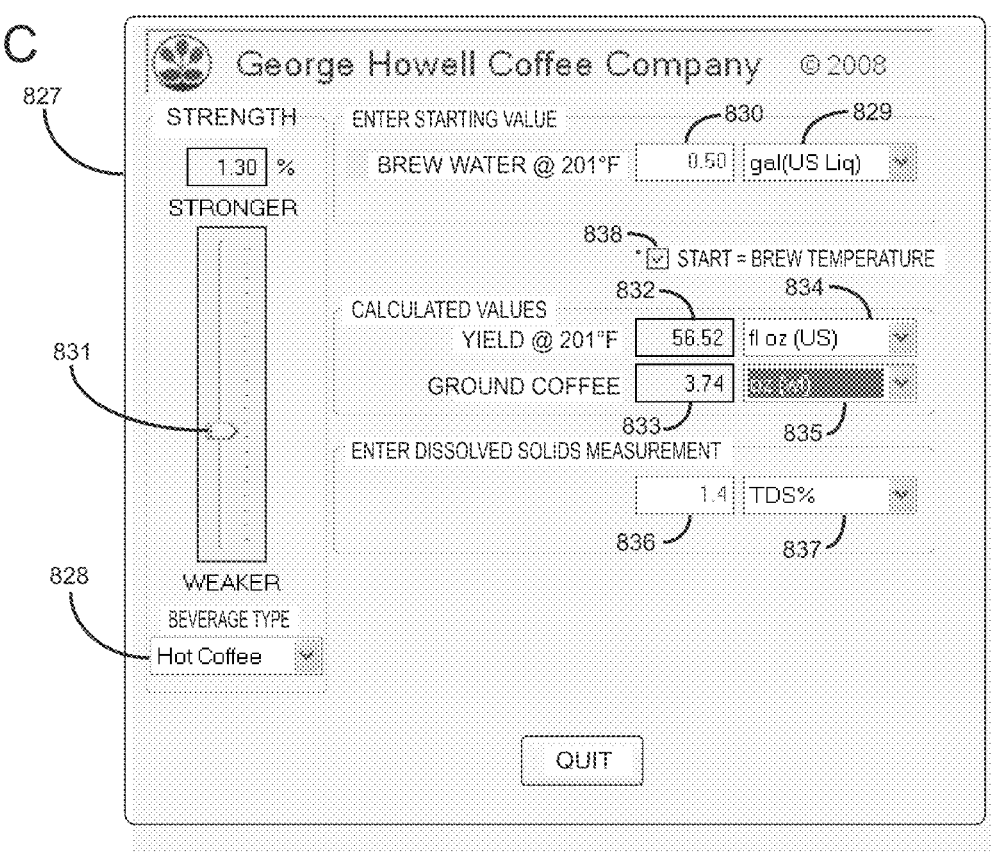
FIG. 8C shows a main window of the disclosed coffee design application operating in the brew water volume mode wherein the user specifies an amount of brew water volume as input.
Figure 8D:
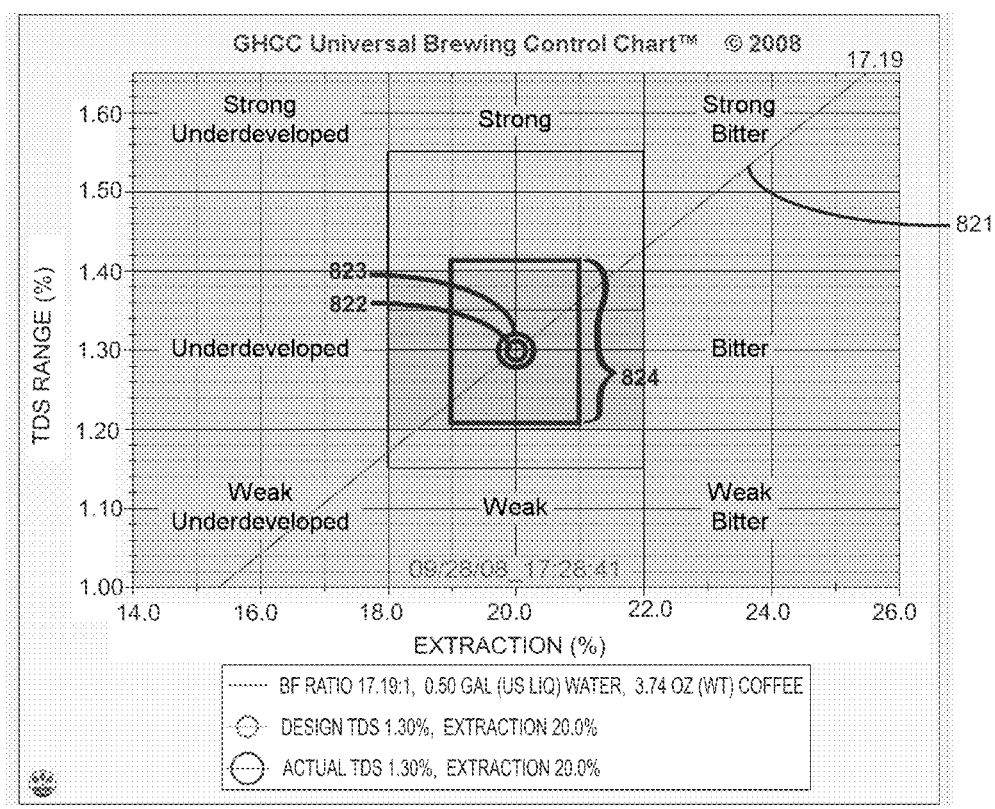
FIG. 8D shows another universal brewing control chart resulting from the disclosed coffee design application operating in the brew water volume mode.
Figure 8E:
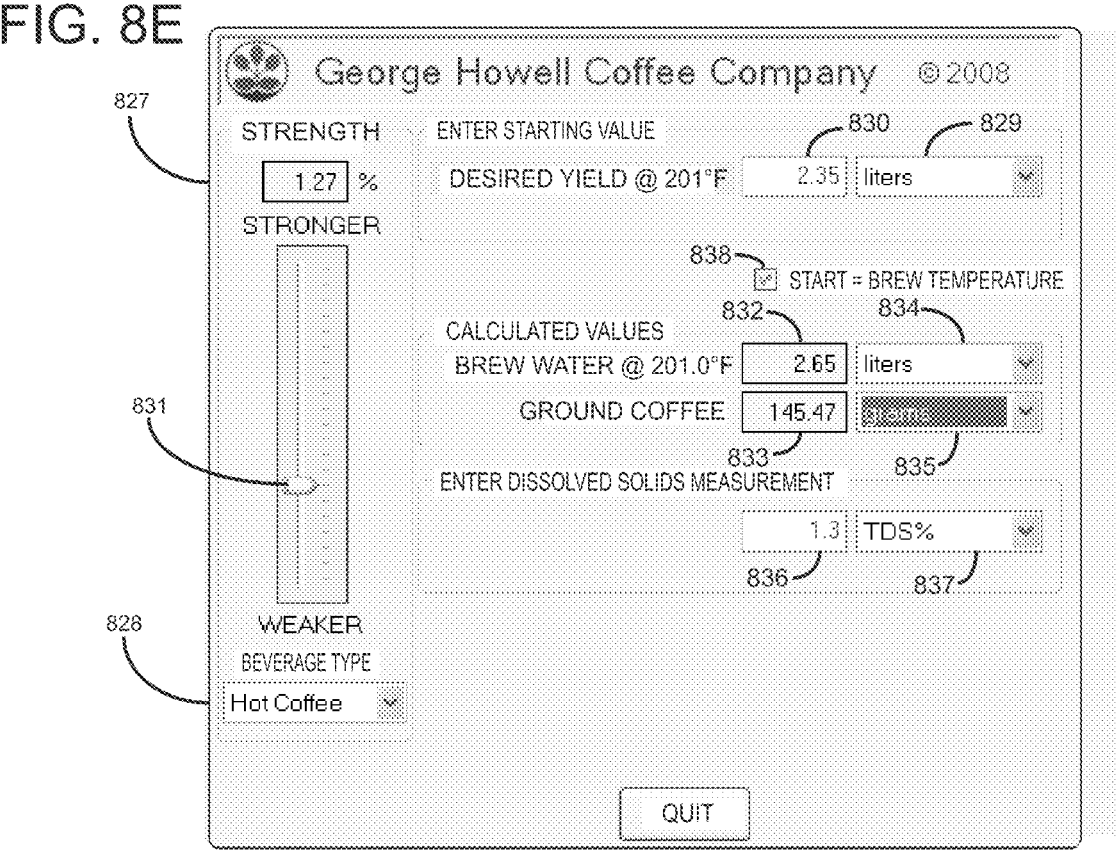
FIG. 8E shows the main window of the disclosed coffee design application operating in the desired coffee yield mode wherein the user specifies an amount of desired coffee yield as input.
Figure 8F:
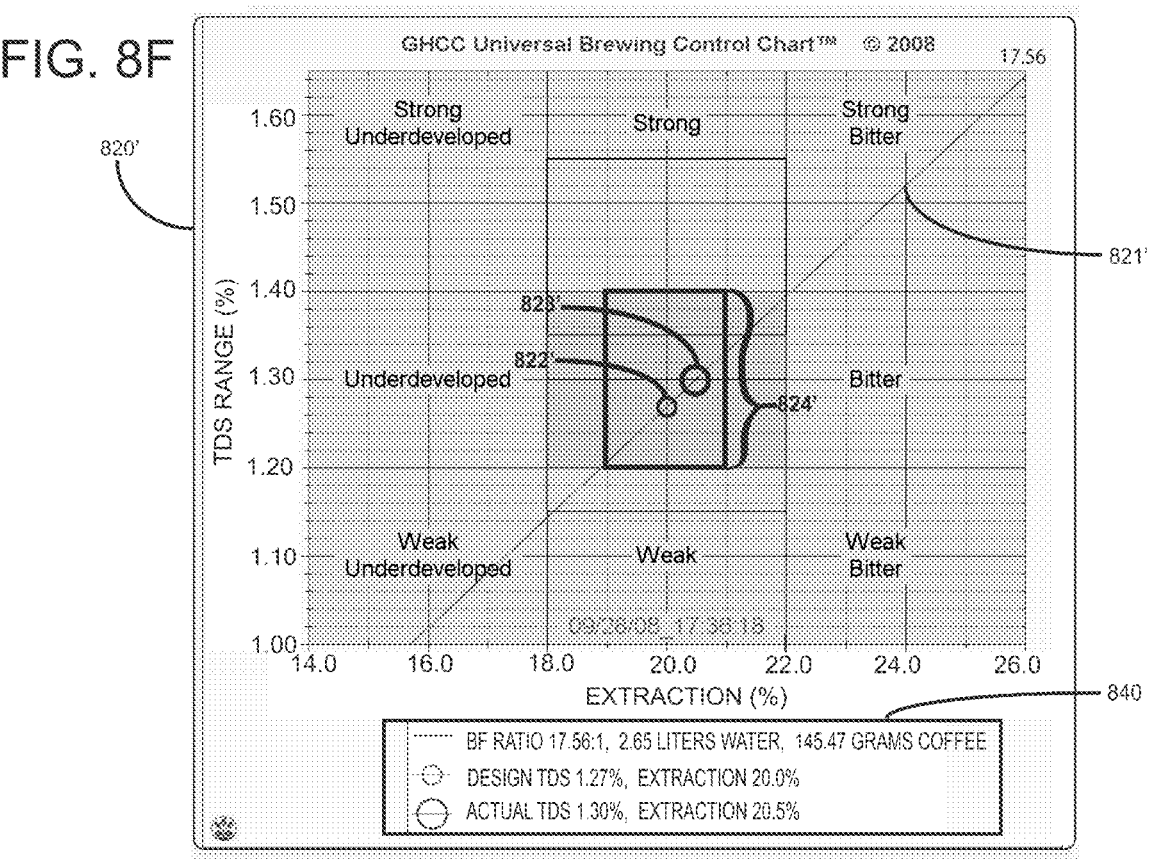
FIG. 8F shows a universal brewing control chart resulting from the disclosed coffee design application operating in the desired coffee yield mode.
Figure 8G:
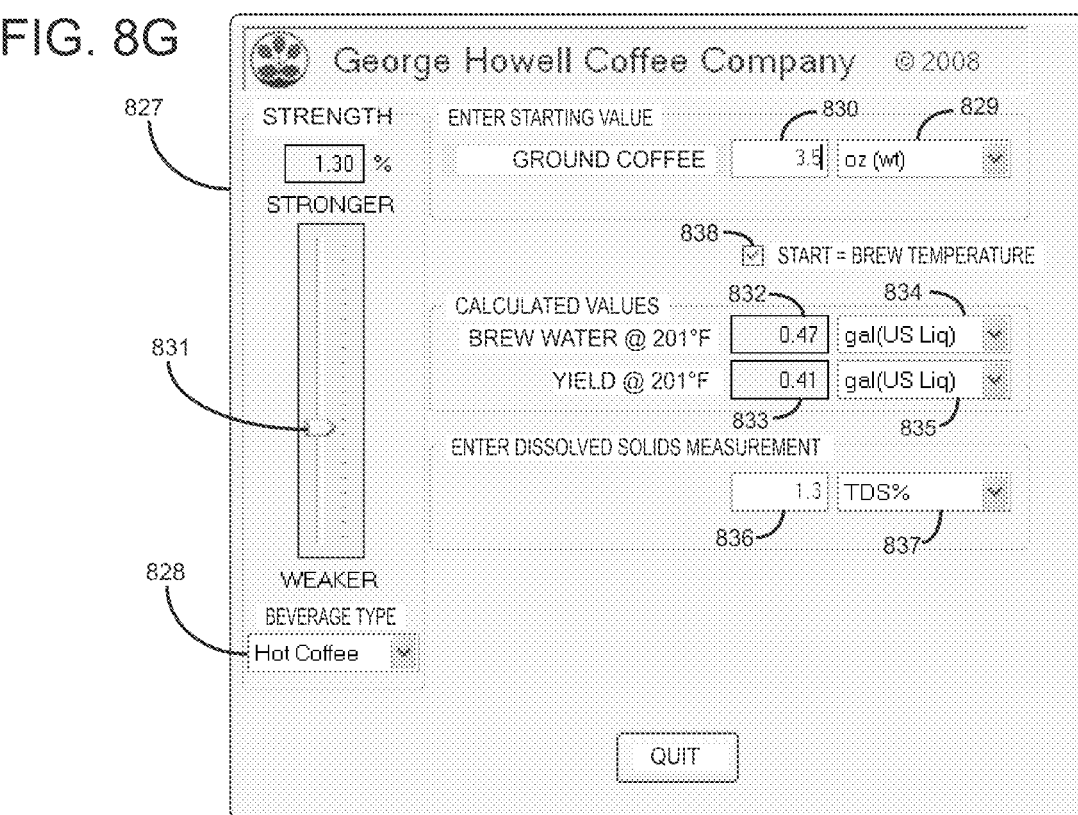
FIG. 8G shows the main window of the disclosed coffee design application operating in the ground coffee weight mode wherein the user specifies an amount of ground coffee weight as input.

FIGS. 8C, 8E and 8G depict screen shots of coffee design application 602 that show different startup modes that are selectable via user Startup Preferences (FIG. 8A), with input selections and corresponding outputs and universal brew formula plotted on charts 8B, 8D and 8F. More particularly, the following design modes are selectable via user startup preferences: 1) brew water volume 2) desired coffee yield and 3) ground coffee weight. The user selects one of the 3 modes as starting input variables in coffee design application 602. In response to this selection and percent TDS as inputs, coffee design application 602 determines the remaining 2 variables as outputs. For example, if the user selects brewing water volume (and selects a % TDS) as the starting variable or mode, coffee design application 602 determines a corresponding coffee yield and coffee ground weight. Alternatively, if the user selects desired coffee yield (and selects a % TDS), then coffee design application 602 determines the required brewing water volume and coffee ground weight needed to achieve this desired coffee yield. This mode is a particularly useful and valuable tool for the coffee trade because it promotes better brewing practice. For example, typically, a brewer may be programmed to dispense water volume in units of gallons, for example one-half gallon. However, the user may be brewing into a commonly available 2.2 or 2.5 liter brewing thermos. Typical yield under these conditions will be approximately 1.7 liters, leaving 0.5 to 0.7 liters in the thermos empty. Coffee brewed in this manner will degrade more rapidly because it cools more quickly, and loses aromatic volatiles that evaporate and condense inside the empty portion of the thermos. Selecting this mode will automatically adjust the required brew water volume and ground coffee required to yield a full batch sized to the thermos is use. Using coffee design application 602, any units of brew water volume, desired coffee yield and ground coffee weight may be selected to suit the actual conditions in the field. Alternatively, if the user selects coffee ground weight (at the desired % TDS strength) as a starting variable or mode, then coffee design application 602 determines the required brewing water volume and resulting coffee yield. This mode is particularly useful for users of pre-ground coffee packets (pillow-packs), where the user selects a fixed coffee portion and desired percent TDS (strength) and application 602 outputs the required brew water volume and resulting yield to brew to gold-cup standards.

Coffee design application 602 generates three windows that help to design and measure brewing parameters. These windows are 1) a startup preferences or brewing preferences window, 2) a main application window and a 3) universal brewing control chart. Coffee design application 602 charts parameters and provides instant feedback so that adjustments, when necessary, can be made quickly and effectively by the user.

FIG. 8A shows a Startup Preferences window 801 that coffee design application 602 generates to enable the user to input operating modes and preferences. Preferences (including changes) are saved automatically between application sessions. The user starts a first design session using the Default Preferences. Upon entering startup preferences window 801, the user selects a preferred design mode in the "Start by Entering" area 802 in the upper left corner of window 801. The user selects one of the three buttons in the "Start by Entering" area 802, namely 1) the Water Volume button 803—Select this option to design by entering the Brew Water Volume amount. In this mode, the software determines or calculates the ground coffee and coffee yield amounts based on user strength TDS selected. 2) the Desired Coffee Yield (Vol) button 804—Select this option to design by entering the Desired Coffee Yield Volume; in this mode, the coffee design application software 202 determines or calculates the ground coffee and brew water amounts based on user strength TDS selected. or 3) the Ground Coffee Weight button 805—Select this option if you are working with a fixed weight of coffee, such as a pillow pack. In this mode, the coffee design application software 202 calculates the brew water volume and coffee yield volume amounts based on user strength TDS selected. The user may select the "Start Value=Last Used" checkbox 806 if the user desires the coffee design application 602 to remember the mode and values used in the last session upon the next startup of the application.

Startup Preferences window 801 includes "Target Settings" area 807 where the user may input Hot Coffee Target Extraction % at box 808. For standard drip brewing of coffee, this default is set to 20 percent extraction, an industry standard "starting point" applicable to a wide range of coffees. For a sweeter cup, the user may try 18.5-19.5 percent, depending on taste preferences, the particular coffee, degree of roast, and grade of grind. Note that extracting to lower targeted levels will require more coffee to achieve the same strength preference. In "Target Settings" area 807, the user may also input the Iced Target Extraction at box 809. For iced coffee, the default target extraction of 19% results in a sweeter cup that is significantly less bitter than a setting of 20% would provide. With higher elevation grown coffees rich in sugars, this recipe often results in a sweet tasting batch without the use of supplemental sweeteners. In "Target Settings" area 807, the user may also input the Iced Target Strength at box 810. For iced coffee, this is the final result of the concentrate after 95-97% all of the ice has melted at the end of the brew. The concentrate is ready to use immediately after the brew cycle has completed. Box 811 indicates the current strength % TDS) range selected for the available design and chart range. If the user selects normal range checkbox 811A, then box 811 displays a strength range of 1.15-1.55%. If the user selects "Extended Range 1" checkbox 811B, then box 811 displays a strength range of 0.4-2.00%. If the user selects "Extended Range 2" checkbox 811C, then box 811 displays a strength range of 0.4-3.6%. These ranges extend the user selectable TDS strength range and also resize the Y-axis on the universal brewing control chart accordingly, and is useful for troubleshooting existing brewing protocols in the field that are out-of-range and off the universal brew chart region of interest Startup Preferences window 801 includes "Water Temperatures" area 812 where the user may input the starting temperature of the water in the brewer at "Start" box 813 and the actual brew temperature of the water in the brewer at "Brew" box 814. The user may select either a degrees F. or a degrees C. scale at temperature scale selection box 812A. For example, the user should select the Brew Temp at Brew box 814 to the programmed setting of the user's brewer (usually 195-202 Deg F.) for light to medium roasted coffees, slightly lower, i.e., 195 Deg F. for dark roasted coffees. The user may enter the start temperature at Start Temperature box 813 to what may typically be in use at home, which should be equal to either TAP water temperature or room temperature (i.e., for bottled water). Using the start and brew temperatures specified, application 602 determines the actual brew water volume and ground coffee weight required to maintain the correct brew formula ratio, a common cause of error when trying to transfer brew formulas from a commercial to a home brewer for example.

Preferences window 801 further includes a "Chart Settings" area 815 for setting preferences in the universal brewing control chart that coffee design application 602 generates. In one embodiment coffee design application 602 may allow the displaying of stored or custom regions of interest for optimum balance to be overlaid onto the universal brewing control chart. Coffee taste preference "regions" have been previously defined by different organizations (i.e. Midwest Research Institute (MRI), Coffee Brewing Center (CBC), Norwegian Coffee Center (NCC) as the "Optimum Balance" regions, or, as shown, other custom regions may be added to the chart based on individual preferences found to be appropriate for particular coffees, roast styles, and or customer surveys. Such custom regions need not be rectangular, as shown, but may be any shape including three dimensional, exhibiting preferences in percentile categories. Selecting the "Show Region Labels" checkbox 816 instructs coffee design application 602 to generate a label identifying the region of interest. Selecting the "Show Taste Labels" checkbox 817 instructs the coffee design application 602 to generate a Universal Brewing Control Chart that displays taste defect labels (i.e., bitter or under-developed). Selecting the "Enable Zoom/Pan" checkbox 818 instructs coffee design application 602 to generate a Universal Brewing Control Chart on which the user may use mouse and/or trackpad controls to zoom/pan the Universal Brewing Control Chart along with its axis. The final universal brewing control chart as configured, plotted and labeled may be saved in any commonly available formats (such as jpeg, png, bmp, emf, gif, tif), emailed, entered into a database, electronically shared, and or printed on demand. Upon completion of entering input preferences and settings in startup preferences window 801, the user may select Done box 819.

After the Startup Preferences have been selected as described above, the user completes the brewing protocol design process in the coffee design application 602 in the Main Application Window shown in FIG. 8C. More details on using the Main Application Window discussed below with reference to FIG. 8C. However, before discussion Main Application Window in detail, it is helpful to first discuss the Universal Brewing Control Chart of FIG. 8B that coffee design application 602 produces. Coffee design application 602 performs all calculations and plots a brewing control chart dynamically and in real time as you change the % TDS strength preference slider control. Coffee design application 602 converts between different types of units instantly and accurately, and allows for mixed units (i.e., brew water in gallons, coffee yield in liters). Coffee design application 602 draws a custom brew formula line on a universal brewing control chart using any combination of selected units in weight and or volume, without restrictions to fixed portions. Application 602 also provides a relative indication of designed recipe to the measured results, in reference to a number of internationally recognized "optimum" brewing ranges. Application 602 further provides a means to troubleshoot current brewing protocols, measure and plot results which immediately identify portioning and extraction errors, and provides a means to correct them. The appearance of the Main Design Window of FIG. 8C depends on the variable the user selected to enter as the INPUT data in the Startup Preferences window 801 of FIG. 8A. Coffee design application 602 displays the computed OUTPUT data immediately below in the next group box of the window, and plots the results on the Universal Brewing Control Chart dynamically and in real time in a charting window seen in FIG. 8B. The completed data and universal brewing control chart as configured, labeled and plotted on the Main Application Window may be saved, recalled, electronically shared, printed or emailed. Each "recipe" may be stored separately, or in one embodiment of the application 602, as part of a database residing within the application or as part of a shared networked database application.

FIG. 8B shows a universal coffee brewing control chart 820 that includes a representative coffee brew formula line 821. The Universal Brewing Control Chart plots the actual design point 822 (small circle) and measured results 823 (large circle) from input data and % TDS measurements from the disclosed coffee refractometer. FIG. 8B shows a typical universal coffee brewing control chart 820, taken from the brew formula discussed below.

FIG. 8B shows the desired brew formula line as brew formula line 821. The brew formula line 821 represents the ratio (17.08:1) of water to coffee by weight used to brew the coffee. The resulting TDS of the brewed coffee will be determined by the brew formula, as well as other factors (temperature, grade of grind, dwell time, and turbulence). The final % TDS measurement 823 may then be followed down to the X-axis, to see how close the results (19.8%) came to the design target extraction (20.0%). The small circle 822 on the Brew Formula line shows the selected strength design target at the default extraction (20%). The larger circle 823 on the brew formula line 821 shows the actual resulting extraction and strength determined by measuring and inputting the TDS % of the brewed coffee into coffee application 602 as a total dissolved solids measurement. The actual resulting extraction and strength are plotted as a result of the TDS % measurement on a specialized coffee refractometer disclosed and discussed below in more detail.

Universal brewing control chart 820 includes a number of coffee design target regions of interest. Chart 820 shows the George Howell Coffee Company (GHCC) suggested target region of interest as region of interest 824 for optimum balance. Chart 820 also shows a Midwest Research Institute region of interest 825. Chart 820 further shows a target region of interest 826 defined by the Norwegian Coffee Center.

FIG. 8C shows the main application window 827 of coffee design application 602. As discussed above, depending on the initial preference settings, application 602 may be used to design coffee brew processes by a 1) a water volume mode, 2) a coffee yield mode or 3) a ground coffee mode. Planning a brew from the starting water volume is now discussed, namely the water volume mode. The Startup Preferences discussed earlier set up the main window for this water volume mode, including brew water temperature to match the brewer boiler setting in use. The brew water volume is first calibrated, according to the brewer manufacturer specifications, to dose correctly the amount of water programmed as the starting brew water volume. The user then performs the following coffee design steps:

1. Select Hot Coffee in the Beverage Type drop-down menu 828 in the lower left-hand corner of main application window 827.
2. Enter the preferred Brew Water units in the drop-down menu 829 next to the Water Volume field 830, and enter the Water Volume in the Water Volume field 830. For example, the user may enter a brew water volume value of 0.50 gal. in Water Volume field 830.
3. Select the preferred Strength TDS % with the slider 831 on the window's left side. In response to the above described user design inputs, application software 602 determines the brew formula and the corresponding required Ground Coffee weight and final Coffee Yield. Coffee design application 602 then displays the determined Ground Coffee weight at Ground Coffee weight box 833 and displays the final Coffee Yield at Coffee Yield box 832. Final values, including the brew formula ratio, are also displayed in the legend of the brewing control chart. The units are selectable by the user at units select boxes 834 and 835. In this example, the resultant yield is 56.52 fl oz (US) and the ground coffee weight is 3.75 oz (wt.) The coffee design application 602 draws the brew formula curve 821 as seen in the universal coffee brewing control chart of FIG. 8D. Coffee design application 602 also plots the target Strength TDS 822 at the pre-set target extraction of 20%.
4. If not done earlier, the user may enter the preferred units of measure in the two output fields, namely Coffee Yield volume 834 and Ground Coffee weight 835 of FIG. 8C. Alternatively, the user may convert these units to any desired units using boxes 834 and 835.
5. After brewing in accordance with the above parameters, the user may test the total dissolved solids (TDS) using the disclosed coffee refractometer. The user may enter the measured % TDS in the Dissolved Solids Measurement field 836 after selecting TDS % at box 837 as the instrument readout mode. Alternatively, coffee design application 602 will provide a conversion estimate for TDS % using box 837 that may be set to ppm or BRIX if another TDS instrument or refractometer provides readings in those units.
6. The user may use a File>Save menu selection to save the brew formula, chart and portion plan, and may print the same if desired.

To summarize, in the above example, beverage type was set to Hot Coffee, brew water volume was set to 0.50 gallons, and the strength slider 831 was set to 1.3% as the desired coffee strength. Coffee design application 602 determines the brew formula ratio, the required ground coffee in oz-wt and the resulting brewed coffee yield in fl-oz volume. Brew temperature was the same as start temperature at 201 Deg F.

FIG. 8E shows the main application window 827 of coffee design application 602. As discussed above, depending on the initial preference settings, application 602 may be used to design coffee brew processes by a 1) a water volume mode, 2) a coffee yield mode or 3) a ground coffee mode. Planning a brew by specifying the second mode, namely, coffee yield as input, is now discussed as coffee yield mode.

Traditionally, brew formulas have been developed using a pre-set volume of brew water as part of the brew recipe. For example, a one (1) gallon batch meant setting the brewer for one gallon of brew water, and using approximately 7.5 ounces coffee (i.e., the gold-cup standard for 1.3% TDS). However, this method results in a final yield of approximately 112-fluid ounces, leaving about 16-fl oz empty in the brewing vessel. In the Desired Yield mode, the disclosed coffee design application 602 enables the user to specify one (1) gallon of finished coffee to fill the brewing vessel completely. In one embodiment, coffee design application 602 determines exact portions of brew water and ground coffee required, for example 1.13 gallons of brew water and 8.5 ounces of coffee. This design mode allows the user to specify the finished yield needed to fill a brewing thermos, rather than leave a significant percentage empty. Units can be mixed in any combination (brew water in gallons, yield in liters), and coffee design application 602 determines the required results in the units specified. For example, for a 2.5 liter thermos, 0.75 gallons brew water and 5.6 ounces of coffee will yield exactly 2.5 liters of finished coffee. To ensure accurate portions of water and coffee, coffee design application 602 takes into account the water lost in the spent basket and the volume of water required as a function of temperature. The brew basket refers to a vessel (not shown) that holds coffee grounds in the correct depth and area in the brewer for proper wetting and extraction during the coffee brewing process. The user selects Startup Preferences window 801 of FIG. 8A and then selects Desired Coffee Yield button 804. The user returns to the main application window 827 of FIG. 8E and enters the desired coffee yield into Desired Coffee Yield box 830 as shown in FIG. 8E. The user may then follow the coffee design method steps below:

1. Set the Beverage Type drop-down menu 828 [in the lower left corner of main application window 827] to select the Hot Coffee charting range.
2. Select the preferred units of measure of the Desired Yield in the drop-down menu 829 next to the Desired Yield field box 830, and enter the Desired Yield for the finished coffee in Desired Yield field box 830. For example, the user may select liters in box 829 and 2.35 in box 830.
3. Select the preferred units of measure if necessary for the two calculated fields at Brew Water Volume unit selection box 834 and Ground Coffee Weight unit selection box 835. In this particular example, coffee design application 602 determines the required Brew Water Volume in liters and the Ground Coffee weight required in grams. When using a commercial brewer, the user should check Start=Brew Temperature box 838 to indicate that the starting temperature is equal to the brewing temperature.
4. Select the preferred Strength with the slider 831. For example, the user may select a strength of 1.27 TDS % in this example.
5. After brewing a batch of coffee under the input conditions above, the user may measure the total dissolved solids in the batch of coffee from a sample thereof. The user places a sample of the brewed batch in the disclosed coffee refractometer discussed in more detail below. The coffee refractometer measures Total Dissolved Solids in percent (%). The user takes a TDS reading from the coffee refractometer and enters the measured % TDS in the "Enter Dissolved Solids Measurement" field or box 836.
6. Use the File>Save menu selection to save the brew plan, and print if desired.

This "Desired Coffee Yield" design mode facilitates better coffee brewing practice in a number of ways. For example, in this design mode, application 602 determines or calculates the coffee and water portions required to nearly fill the brewing vessel completely. This mode also reduces the amount of air in a thermos or other coffee brew receptacle, and reduces the loss of aroma producing volatiles, while increasing the volume of hot coffee brewed. The additional thermal mass of coffee keeps the thermos hot longer, and can increase hold times by up to 10-15 minutes per batch. This mode may also reduce the frequency of brewing, making a coffee brewing operation more efficient. This mode may allow brewing larger batches that inherently reduces portioning errors. In the "Desired Coffee Yield" design mode in the example of FIG. 8E, the Beverage Type is set to Hot Coffee at Beverage Type drop down menu 828, and Desired Yield is set to 2.35 Liters in boxes 830, 832 for a 2.5 Liter Thermos receptacle. Strength slider 831 is set to 1.27% TDS. The disclosed coffee refractometer is used to test a sample of the brewed coffee. In this example, the coffee refractometer measures a TDS value of 1.3%, which is entered by the user at Enter Dissolved Solids Measurement input box 836. In response to entering the TDS value, coffee design application 602 plots a universal coffee brewing control chart 820' as shown in FIG. 8F. Universal coffee brewing control chart 820' shows the brew formula, namely a brew formula line 821', as a brew formula ratio of 17.56 to 1. Coffee design application 602 plots a small circle 822' that indicates the selected strength coffee design target at the default extraction (20%). The larger circle 823' on brew formula line 821' indicates the actual resulting extraction and strength determined by measuring the TDS % of the brewed coffee sample with the disclosed coffee refractometer and inputting the measured TDS % into coffee design application 602 as a total dissolved solids measurement. Since the measured coffee results are within 0.5% of the target extraction (solubles yield) of the design target, no further adjustment is required in this example. The final coffee design recipe values are also shown in the chart Legend 840, at the bottom of the chart 820'.

FIG. 8G shows the main application window 827 of coffee design application 602. As discussed above, depending on the initial preference settings, application 602 may be used to design coffee brew processes by a 1) a water volume mode, 2) a coffee yield mode or 3) a ground coffee mode. Planning a brew by specifying the third mode, namely ground coffee weight as input, is now discussed as ground coffee weight mode.

Design by ground coffee weight is a commonly used in high volume feeder establishments using pre-measured, pre-ground pillow packs. While it is not preferable to pre-grind coffee for freshness reasons, this mode is provided to address such feeder establishments, so they can improve their coffee brewing practices to internationally accepted standards.

The user selects Startup Preferences window 801 of FIG. 8A and then selects Ground Coffee Weight button 805. The user returns to the main application window 827 of FIG. 8G and enters the ground coffee weight into ground coffee weight box 830 as shown in FIG. 8G. For example, if the weight of a pre-ground coffee pillow pack is 3.5 oz, then the user selects the unit ounces in unit selection box 829 and inputs 3.5 into box 830 as shown. The user may then follow the coffee design method steps below:

1. Select Hot Coffee in the Beverage Type drop-down menu 828 in the lower left corner of main application window 827.
2. Select the preferred unit of measure in the drop-down menu 829 next to the Ground Coffee field 830, and enter the weight in the Ground Coffee field 830.
3. Select the preferred units of measure if necessary for the two calculated fields, namely Brew Water Volume and Yield. Coffee design application 602 determines or calculates the required Brew Water Volume and the final coffee Yield volume in the units selected. Start Temperature=Brew Temperature is checked at checkbox 838.
4. Select the preferred Strength with the slider 831. In this example, the user engages slider 831 to select a strength of 1.3%.
5. After brewing coffee in accordance with the determined parameters, the user then employs the disclosed coffee refractometer to measure the total dissolved solids, TDS, of a sample of the brewed coffee. The user enters the measured % TDS in the Enter Dissolved Solids Measurement field 836.
6. Use the File>Save menu selection to save the brew plan, and print if desired.

This example illustrates how to design to desired strength protocols using fixed ground coffee packets by weight. Coffee design application 602 calculates the required brew Water Volume and Yield volume of coffee in the units selected. The Beverage Type drop-down menu 828 was set to Hot Coffee. Ground Coffee was set to the packet size of 3.5 ounces weight. Strength slider was set to 1.30% TDS. Dissolved Solids were measured and entered at 1.3%

Figure 8H:
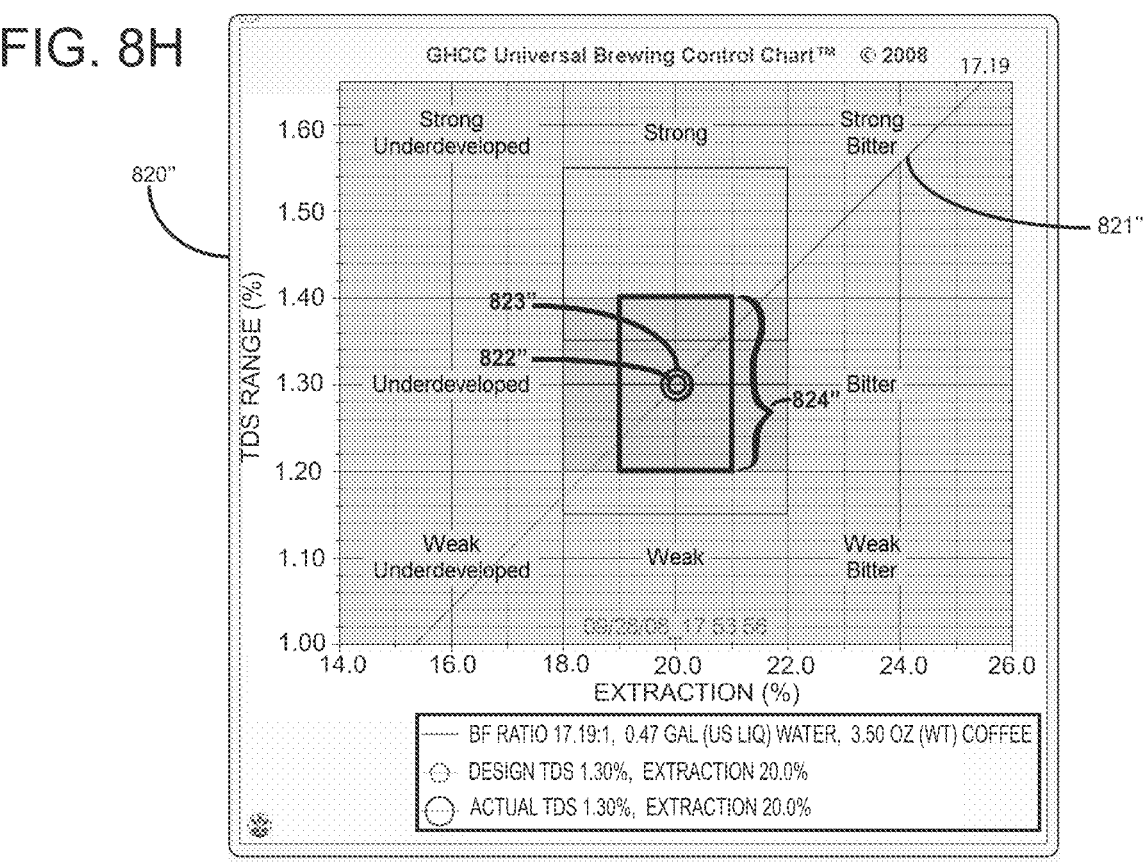
FIG. 8H shows a universal brewing control chart resulting from the disclosed coffee design application operating in the ground coffee weight mode.

Coffee design application 602 draws a universal coffee brewing control chart 820'' as shown in FIG. 8H. In FIG. 8H, box 824'' represents the desired target region and line 821'' represents the particular brew formula ratio, namely 17.19 to 1, in this particular example that employs 0.47 gallons of water and 3.5 oz (wt) of coffee to brew a batch of coffee. Small circle 822'' represents the desired design point on brew formula line 821'', while large circle 823'' represents the actual coffee design point determined in response to the measured TDS % of the brewed coffee batch measure in the disclosed coffee refractometer. Region 824'' is the particular region of interest on the brew control chart of FIG. 8H. This design mode is useful for users of pre-ground and pre-weighed fixed packs of ground coffee wishing to improve their coffee brewing protocols by providing a means to reprogram their brewers to brew to gold-cup standards, even though fixed weight packs have been provided.

Figure 8I:
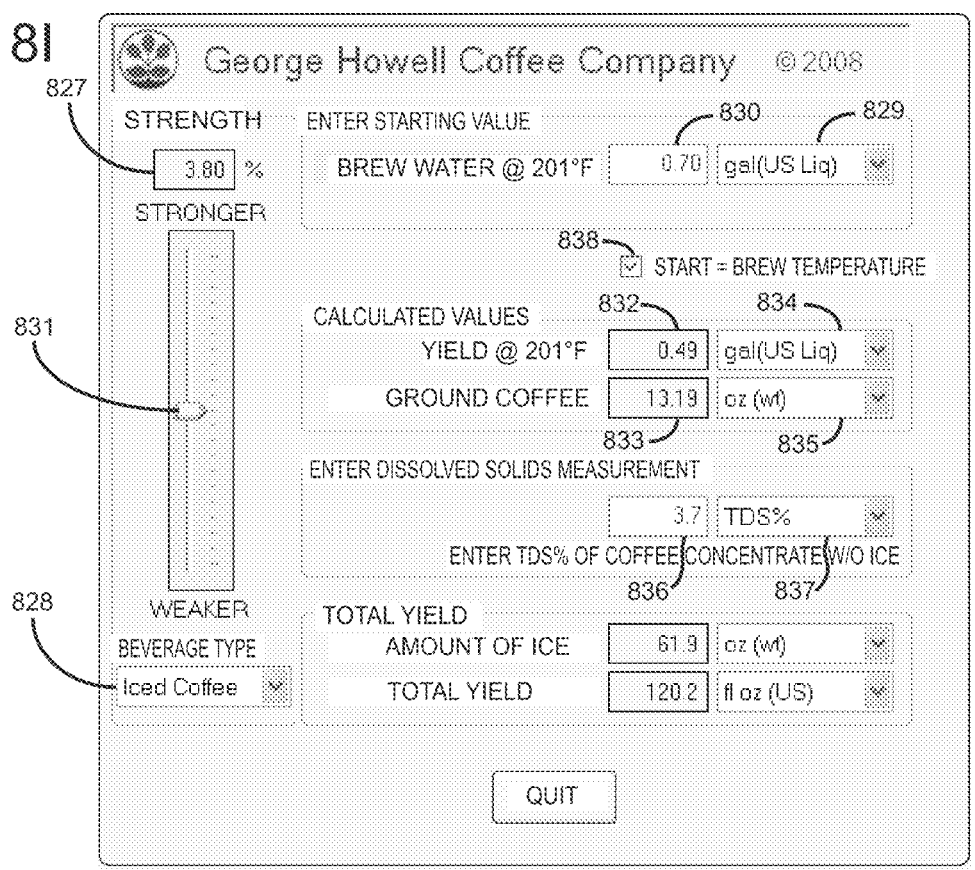
FIG. 8I shows the main window of the disclosed coffee design application for a iced coffee beverage wherein the disclosed coffee design application operates in the brew water volume mode wherein the user specifies an amount of brew water volume as input.
Figure 8J:
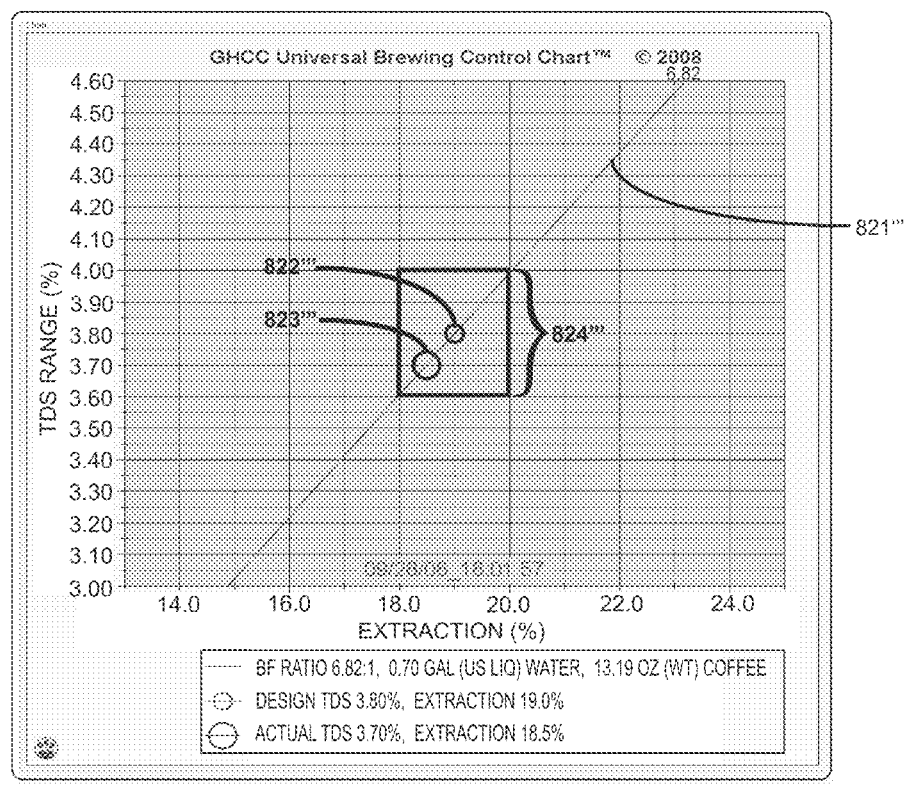
FIG. 8J shows a universal brewing control chart resulting from the disclosed coffee design application operating in the brew water volume mode for an iced coffee beverage.

FIG. 8I shows the main application window 827 of coffee design application 602 which is also useful in designing coffee concentrates. This example shows an iced coffee design, where the user selects iced coffee in Beverage Type drop-down menu 828. The coffee design application 602 will design coffee extraction protocols for Iced Coffee Concentrate, to be brewed fresh and directly over ice. Coffee design application 602 calculates coffee concentrate TDS strength both before and after ice is melted. The process is designed to allow approximately 95% to approximately 97% percent of the ice to melt at brew completion time, so that the finished concentrate is cold, and ready to serve immediately after brewing. In one embodiment, the complete brewing cycle takes only 5-6 minutes, typically. Care should be taken using this mode to choose portions that will not overload nor overflow the brew basket. For example, a 0.5-1.0 gallon brewer may be able to brew 7-9 ounces of ground coffee, but could overflow the brew basket if more ground coffee is used. Generally, a 1.5 gallon brewer can accommodate up to 12-14 ounces ground coffee. Design by coffee weight mode is supported in this embodiment, to ensure such limitations are adhered to, and application 602 determines the required brew water volume, concentrate yield, and weight of ice required. In this example, the user sets the coffee brew strength to 3.8% using slider 831. The user employs brew water volume as the starting value in Enter Starting Value box 830. The units are gallons in unit selection box 829. In this example, it is assumed that a typical 1.5 gallon brewer is being used. The brewer is programmed to dispense 0.7 gallons, yielding approximately a half-gallon (0.49 gal) of coffee at 3.7% TDS. The coffee is brewed into an open top container containing 62 ounces-weight of ice, then stirred and covered. The resulting concentrate is after serving over ice in a glass filled two-thirds will be about 1.5-1.8% TDS. Total concentrate yield is just under one gallon. This serves approximately sixteen 16-oz servings (7.5 fl oz concentrate over approximately 8 oz-wt ice). Coffee design application 602 plots the resultant brew formula ratio curve 821''' as seen in FIG. 8J. Coffee design application 602 also plots the target coffee design point as small circle 822'''. After the user measures the total dissolved solids TDS % with the disclosed coffee refractometer and inputs the TDS % value, for example 3.7%, in box 836, application 602 plots the actual coffee design point at large circle 823''' on brew formula ratio line 821'''.

Figure 9A:
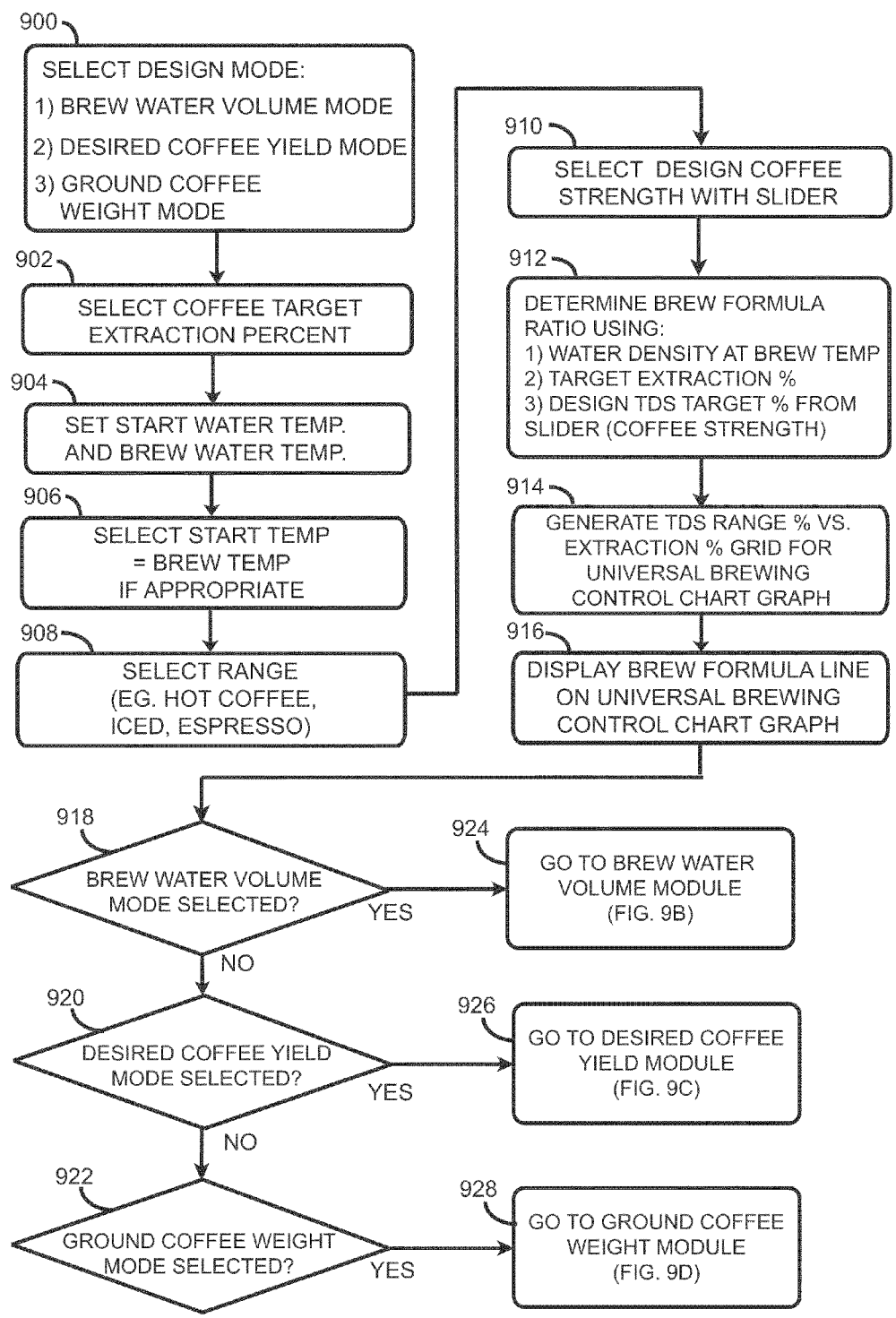
FIG. 9A is a flowchart showing process flow in the disclosed coffee design methodology.

FIG. 9A is a flowchart that shows process flow in the methodology that the disclosed information handling system 600 employs. In one embodiment, when loaded into system 600, coffee design application 602 of computer program product 608 enables system 600 to carry out this methodology. System 600 asks the user to select from the following design coffee modes: 1) brew water volume mode 2) desired coffee yield mode and 3) ground coffee weight mode, as per block 900 of the flowchart of FIG. 9A. System 600 asks the user to select a coffee target extraction percent, as per block 902. System 600 receives the user's coffee target extraction percent selection as input to the coffee design process.

System 600 asks the user to set the starting water temperature and the brewing water temperature, as per block 904. System 600 receives the user's starting water temperature and brewing water temperature as inputs to the coffee design process. System 600 queries the user to determine if the starting temperature equals the brewing temperature, as per block 906. System 600 queries the user to select a beverage type, namely hot coffee, iced coffee or in another embodiment, espresso, as per block 908. The Beverage Type drop-down menu pre-sets 828 are used to adjust the brewing and chart areas of solubles concentration (% TDS Strength) and solubles yield (% Extraction) to the appropriate ranges commonly used for brewing the selected types of beverage(s). System 600 receives the user's Beverage Type selection as input to the coffee design process. System 600 presents a slider tool 831 to the user to enable the user to select a design coffee strength, as per block 910. For example, the user may select a strength of 1.3% with the slider tool, or may also use arrow keys, touch screen controls or other methods for setting the input value. System 600 receives the user's selection of coffee strength as input to the coffee design process.

System 600 determines the brew formula ratio using 1) weight of water, determined from the volume of the water at the prescribed brewing temperature 2) the target extraction percent % solubles yield) and 3) the design TDS target strength (% solubles concentration) from the slider control (i.e. coffee strength), as per block 912. The final brew formula ratio is equal to the weight of water divided by the weight of coffee as determined by the above parameters, and remains the same regardless of the brew batch size. System 600 generates a universal control chart graph including a grid showing TDS range (%) on the y axis vs. coffee extraction (%) on the x axis, as per block 914. Using the brew formula ratio determined in block 912, system 600 plots and displays on the universal control chart graph the brew formula line that represents the brew formula ratio.

System 600 performs tests to determine if the user selected 1) brew water volume mode, 2) desired coffee yield mode, or 3) ground coffee weight mode at decision blocks 918, 920 and 922. If the user selected 1) brew water volume mode, then process flow continues to the brew water volume module of FIG. 9B, as per block 924. If the user selected 2) desired coffee yield mode, then process flow continues to the desired coffee yield mode of FIG. 9C, as per block 926. If the user selected 3) ground coffee weight mode, then process flow continues to ground coffee weight module of FIG. 9D, as per block 928.

Figure 9B:
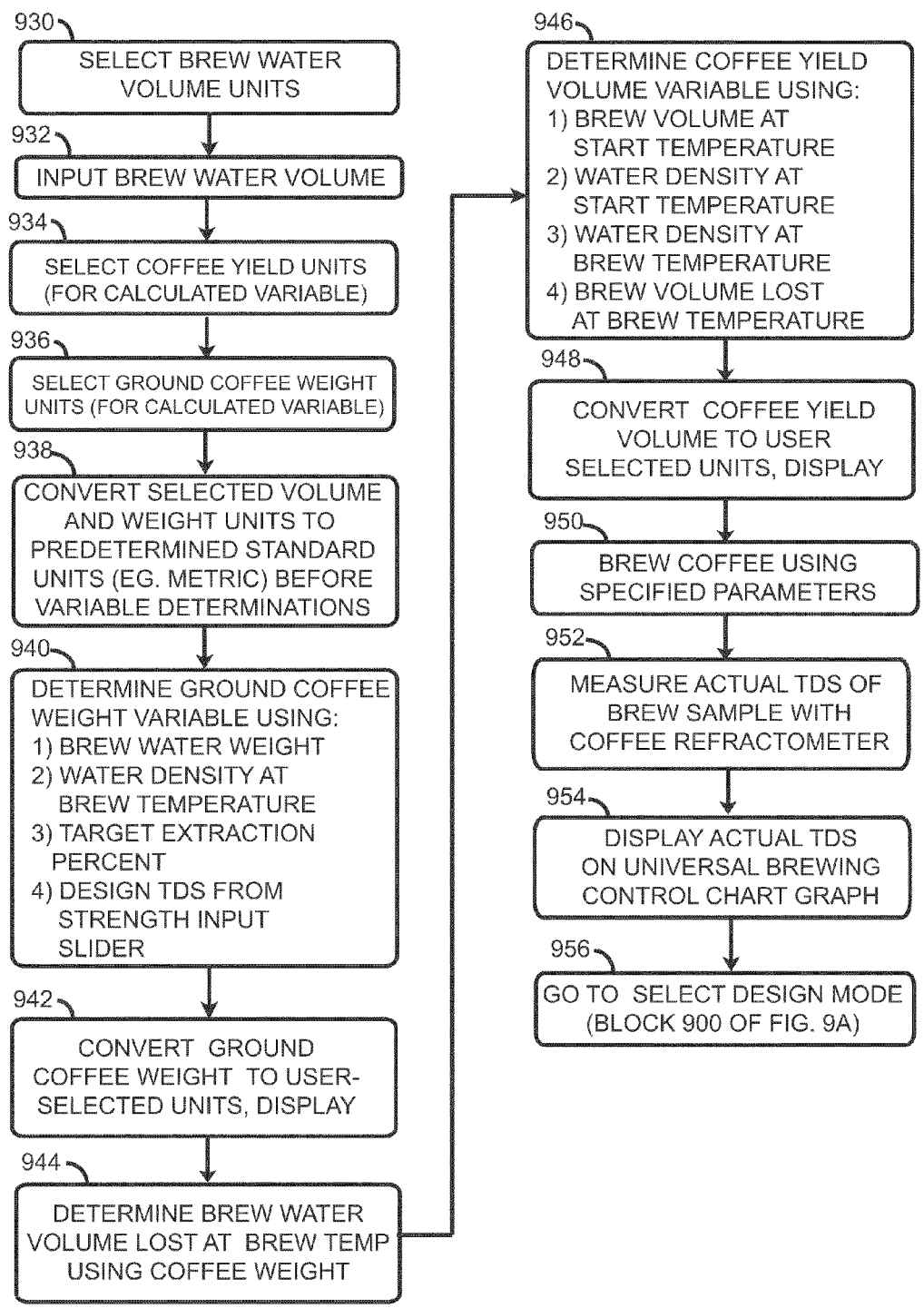
FIG. 9B is a flowchart that depicts process flow in a brew water volume mode of the disclosed methodology.

FIG. 9B shows process steps that system 600 performs when the user selects the brew water volume mode. In one embodiment, coffee design application 602 instructs system 600 to carry out these process steps. System 600 asks the user to select brew water volume units, as per block 930. In one embodiment, this is achieved by a pull-down menu or unit selection box with different volume unit selections. System 600 receives the user's brew water volume unit selection as input to the coffee design process. System 600 also asks the user to select the brew water volume, as per block 932. System 600 receives the selected brew water volume as input to the coffee design process. System 600 asks or allows the user to select units for the coffee yield variable that the system determines in response to user input, as per block 934. The selected units may be milliliters, liters, fluid ounces, quarts or gallons, for example. Coffee yield is a determined or calculated variable that is a function of user input selections. System 600 asks or allows the user to select units for the ground coffee weight variable that the system determines in response to user input, as per block 936. The selected units may be grams, ounces or pounds, for example. Ground coffee weight is a determined or calculated variable that is a function of user input selections.

System 600 converts the selected volume and weight units to predetermined internal standard units (e.g. metric units) before performing variable determinations in response to user input, as per block 938. Calculations are performed within system 600 in these standard units and then converted later to the units selected by the user for display purposes. System 600 determines the ground coffee weight variable using 1) brew water weight 2) water density at brew temperature 3) target extraction percent and 4) design TDS from the strength input slider, as per block 940. More particularly, coffee design application 602 of system 600 employs EQUATION 2 to determine the coffee weight variable:

$$\text{coffee weight(g)} = \text{water weight(g)} / (E\% * (1/TDS\% - 0.01) + \text{waterdensity@brew temp(g/ml)} * \text{waterLost(ml/g)}) \quad \text{Equation 2}$$

wherein E % is Extraction percent. System 600 converts the determined ground coffee weight variable to the user-selected units and displays the result, as per block 942.

System 600 determines the brew water volume lost at brew temperature using the coffee weight, as per block 944. System 600 determines the coffee yield volume variable using 1) the brew volume at the start temperature, 2) water density at the start temperature, 3) water density at the brew temperature, and 4) brew volume lost at brew temperature, as per block 946. More particularly, coffee design application 602 of system 600 employs EQUATIONS 3 to determine the coffee yield volume variable:

$$\begin{aligned}&1)\ \text{Volume\_Lost\_at\_}T\text{brew(ml)} = \text{waterLost(ml/g)} * \text{coffee weight(g)}\\ &2)\ \text{Yield volume(ml)\_at\_}T\text{brew} = \text{water\_volume(ml)\_at\_}T\text{start} * \text{Density(g/ml)@startTemp/Density(g/ml)@brewTemp} - \text{volume Lost\_at\_}T\text{brew(ml);}\end{aligned} \quad \text{Equation 3}$$

System 600 converts the determined coffee yield volume to the user-selected units and displays the results, as per block 948. The user or other entity then brews coffee using the specified parameters and determined variables or results, as per block 950. The user, other entity or apparatus measures the actual total dissolved solids that the resultant brewed coffee exhibits, as per block 952. For example, the disclosed coffee refractometer may determine the TDS % that a sample of the brewed coffee exhibits. System 600 displays the actual TDS reading on the universal brewing control chart graph, as per block 954. For example, circle 823 of the universal brewing control chart graph of FIG. 8B shows such a display of actual TDS results. Process flow continues back to the select design mode block 900 of FIG. 9A. The user may then again select any coffee design mode desired.

Figure 9C:
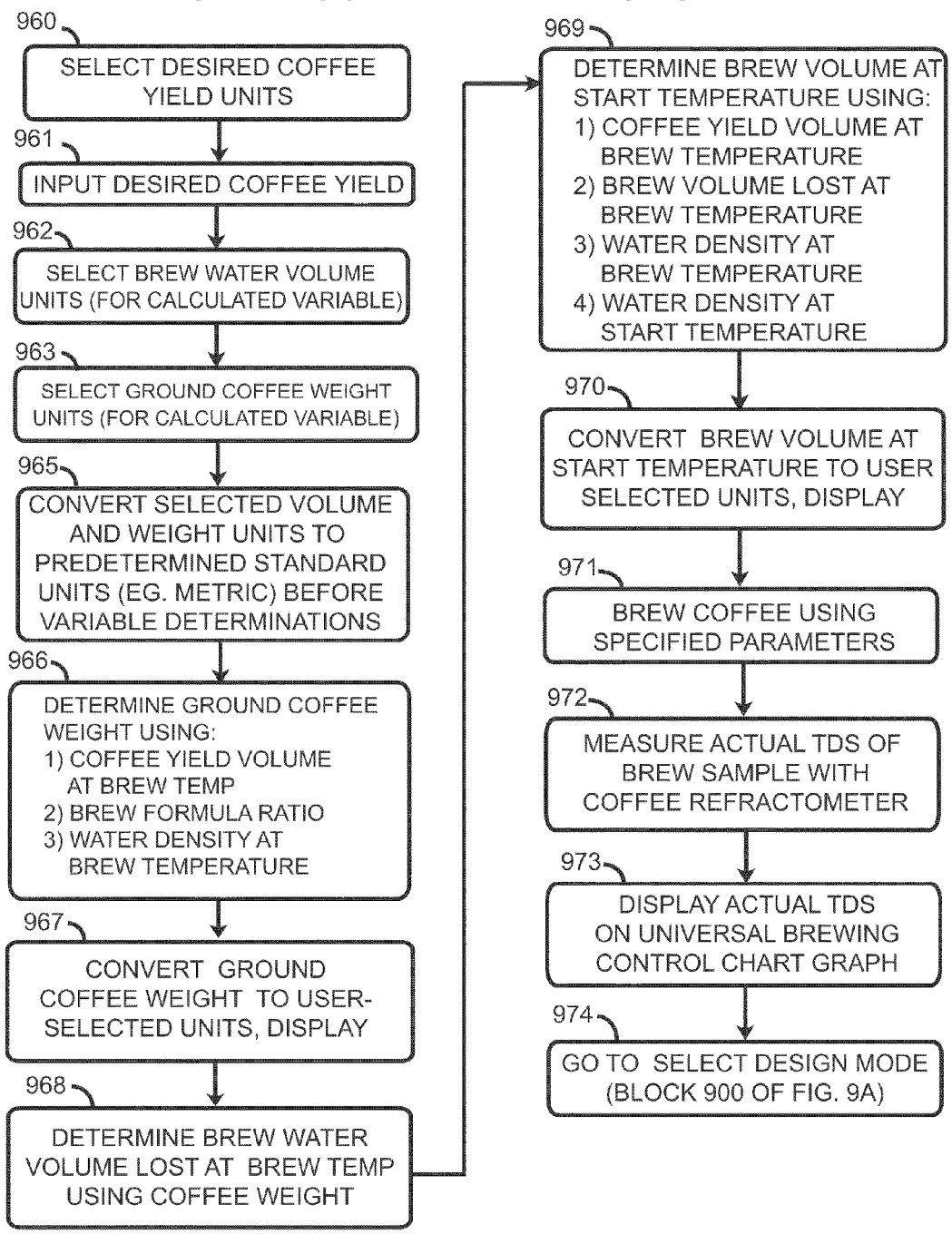
FIG. 9C is a flowchart that depicts process flow in a desired coffee yield mode of the disclosed methodology.

FIG. 9C shows process steps that system 600 performs when the user selects the desired coffee yield mode. In one embodiment, coffee design application 602 instructs system 600 to carry out these process steps. System 600 asks or allows the user to select desired coffee yield units, as per block 960. In one embodiment, this is achieved by a pull-down menu or unit selection box with different desired coffee yield unit selections. System 600 receives the user's desired coffee yield unit selection as input to the coffee design process. System 600 also asks the user to select the coffee yield, as per block 961. System 600 receives the selected coffee yield volume as input to the coffee design process. System 600 asks or allows the user to select units for the brew water volume variable that the system determines in response to user input, as per block 962. The selected units may be milliliters, liters, fluid ounces, quarts or gallons, for example. Brew water volume is a determined or calculated variable that is a function of user input selections. System 600 also asks or allows the user to select units for the ground coffee weight variable that the system determines in response to user input, as per block 963. The selected units may be grams, ounces or pounds, for example. Ground coffee weight is a determined or calculated variable that is a function of user input selections.

System 600 converts the selected volume and weight units to predetermined internal standard units (e.g. metric units) before performing variable determinations in response to user input, as per block 965. Calculations are performed within system 600 in these standard units and then converted later to the units selected by the user for display purposes. System 600 determines the ground coffee weight variable using 1) coffee yield volume at brew temperature 2) brew formula ratio 3) water density at room temperature, as per block 966. More particularly, coffee design application 602 of system 600 determines the ground coffee weight variable using EQUATION 4:

$$\text{coffee(g)} = \text{water weight(g)}/BF \quad \text{Equation 4}$$

System 600 converts the determined ground coffee weight variable to the user-selected units and displays the result, as per block 967.

System 600 determines the brew water volume lost at brew temperature using the coffee weight, as per block 968. System 600 determines the brew volume at start temperature variable using 1) coffee yield volume at brew temperature, 2) brew volume lost at brew temperature, 3) water density at the brew temperature, and 4) water density at the start temperature, as per block 969. More particularly, coffee design application 602 of system 600 determines the brew volume at start temperature variable using EQUATION 5:

$$\text{water volume(ml)@}T\text{start} = (\text{yield\_vol(ml)@\_}T\text{brew} + \text{VolumeLost\_at\_}T\text{brew(ml)}) * \text{Density(g/ml)@brewTemp/Density(g/ml)@startTemp;} \quad \text{Equation 5}$$

System 600 converts the brew volume at start temperature to the user-selected units and displays the results, as per block 970. The user or other entity then brews coffee using the specified parameters and determined variables or results, as per block 971. The user, other entity or apparatus measures the actual total dissolved solids that the resultant brewed coffee exhibits, as per block 972. For example, the disclosed coffee refractometer may determine the TDS % that a sample of the brewed coffee exhibits. System 600 displays the actual TDS reading on the universal brewing control chart graph, as per block 973. For example, large circle 823' of the universal brewing control chart graph of FIG. 8F shows such a display of actual TDS results. Process flow continues back to the select design mode block 900 of FIG. 9A, as per block 974. The user may then again select any coffee design mode desired.

FIG. 9D shows process steps that system 600 performs when the user selects the ground coffee weight mode. In one embodiment, coffee design application 602 instructs system 600 to carry out these process steps. System 600 asks or allows the user to select desired ground coffee weight units, as per block 980. In one embodiment, this is achieved by a pull-down menu or unit selection box with different desired coffee ground weight unit selections. System 600 receives the user's desired ground coffee weight unit selection as input to the coffee design process. System 600 also asks the user to select the ground coffee weight, as per block 981. System 600 receives the selected ground coffee weight as input to the coffee design process. System 600 asks or allows the user to select units for the brew water volume variable that the system determines in response to user input, as per block 982. The selected units may be milliliters, liters, fluid ounces, quarts or gallons, for example. Brew water volume is a determined or calculated variable that is a function of user input selections. System 600 also asks or allows the user to select units for the coffee yield volume variable that the system determines in response to user input, as per block 983. The selected units may be milliliters, liters, fluid ounces, quarts or gallons, for example. Coffee yield volume is a determined or calculated variable that is a function of user input selections.

System 600 converts the selected volume and weight units to predetermined internal standard units (e.g. metric units) before performing variable determinations in response to user input, as per block 984. Calculations are performed within system 600 in these standard units and then converted later to the units selected by the user for display purposes. System 600 determines the brew water volume variable using 1) coffee weight 2) target extraction percent 3) design TDS from strength input slider, as per block 985. More particularly, coffee design application 602 of system 600 determines the brew water volume variable using EQUATION 6:

$$\text{water volume(ml)}=\text{water volume lost(ml)}* \text{Density(g/ml)@brewTemp/Density(g/ml)@startTemp}+ [\text{coffee weight(g)}*E\%*(1/TDS\%-0.01)]/\text{Density(g/ml)@startTemp} \qquad \text{Equation 6}$$

System 600 converts the determined brew water volume variable to the user-selected units and displays the result, as per block 986.

System 600 determines the brew water volume lost at brew temperature using the coffee weight, as per block 987. System 600 determines the coffee yield volume variable using 1) brew volume at start temperature, 2) water density at start temperature, 3) water density at the brew temperature, and 4) brew volume lost at brew temperature, as per block 988. More particularly, coffee design application 602 of system 600 determines the brew water volume lost at brew temperature variable using EQUATION 7:

$$\text{yield volume(ml)@brewTemp}=\text{water\_volume(ml)@startTemp}* \text{Density(g/ml@startTemp/Density(g/ml)@brewTemp}-\text{volumeLost@brewTemp (ml)}; \qquad \text{Equation 7}$$

System 600 converts the coffee yield volume to the user-selected units and displays the results, as per block 989. The user or other entity then brews coffee using the specified parameters and determined variables or results, as per block 990. The user, other entity or apparatus measures the actual total dissolved solids that the resultant brewed coffee exhibits, as per block 991. For example, the disclosed coffee refractometer may determine the TDS % that a sample of the brewed coffee exhibits. System 600 displays the actual TDS reading on the universal brewing control chart graph, as per block 992. For example, large circle 823" of the universal brewing control chart graph of FIG. 8H shows such a display of actual TDS results. Process flow continues back to the select design mode block 900 of FIG. 9A, as per block 993. The user may then again select any coffee design mode desired.

Returning again to the small form factor or hand-held information handling system (IHS) 675 of FIG. 6B, it is noted that IHS 675 receives user input in one spatial orientation or position and outputs results to its display 690 when the user moves or changes the IHS to a second spatial orientation or position. More specifically, the user may use touch screen display 690 to make user selections and provide other input while IHS 675 is in the first position. For example, the user employs touch screen display 690 to select startup preferences such as selecting one of multiple design modes, namely 1) brewing water volume mode, 2) desired coffee yield mode, and 3) ground coffee weight mode. The user may also make other input selections shown in startup preferences of FIG. 8A while IHS 675 is oriented in the first spatial orientation. In response to such input and when the user changes the spatial orientation of the IHS to a second spatial orientation, coffee design application 602 draws a universal brewing control chart such as shown in FIGS. 8B, 8D, 8F, 8H and 8J on display 690. The displayed universal control chart displays the results of user input which may include a TDS % reading from the disclosed refractometer for a brewed coffee sample that is brewed in accordance with the coffee design parameters that coffee design application 602 determines.

In one embodiment, to complete the final plot point on the universal brewing control chart, the actual measured % TDS may be entered when IHS 675 is in either the first or second spatial position. For example, the measured % TDS from the disclosed coffee refractometer may be entered on touch screen display 690 on either the universal brewing control chart on the display while the IHS exhibits the second orientation (such as vertical) or the Main Application window while the IHS exhibits the first orientation (such as horizontal) by using extended touch screen commands that appear on the universal brewing control chart, for example, as buttons or data entry boxes, in a visible layer behind the partially transparent displayed chart.

Generally, IHS 675 receives the user's input selections while IHS 675 exhibits the first spatial orientation while coffee design application 602 receives the first position signal from sensor package 680. When coffee design application 602 of IHS 675 receives the second position signal, indicating that the user has changed the orientation of the IHS 675 to the second spatial orientation, coffee design application 602 senses this signal change and in response determines or calculates the solution to the user inputs, including but not limited to the brew formula, required portions of coffee and water, and draws a universal brewing control chart on display 690.

Specific recipes for any number of brew formula sessions may be stored in the IHS 675 as an integrated database in non-volatile memory 679, and or transmitted to a database via any of a number of wireless protocols, including web-based sharing protocols, or electronically mailed to other users to share, and interactively modify, for example, based on a collaborative approach to establishing a desired brewing protocol. Such recipes may be used to control brewing protocols for an entire installed base of brewing equipment, such equipment being programmable manually or automatically to execute said protocol(s), through a manual, wired or wireless interface, for example, for feeder establishments wishing to maintain a high quality coffee brewing program to ensure consistency from cup-to-cup across its entire installed base of restaurants, cafes or coffee bars.

FIG. 10A shows the disclosed refractometer 1000 that is usable to measure TDS % of a brewed coffee sample by determining the index of refraction of the brewed coffee sample. Refractometer 1000 includes a light source 1005 such as a yellow semiconductor laser that generates 589 nm light in one embodiment. An illumination lens 1010 directs the light from light source 1005 toward prism 1015 as shown. Prism 1015 receives incident light 1017 from light source 1005 as shown. Prism 1015 is a transparent material that exhibits an index of refraction "$n_p$". The user or other entity or apparatus places a coffee brew sample 1020 on prism surface 1025 in preparation for measurement of the index of refraction "$n_s$" that the brew sample 1020 exhibits.

A collection lens 1030 collects light 1032 refracted or reflected by the prism sample interface 1034 and directs that light to a linear photo detector 1035. The purpose of the illumination lens 1010 is to direct light from light source 1005 to prism 1015. More specifically, the purpose of illumination lens 1010 is to form a focusing beam or cone of light incident upon the prism-sample interface 1034 that ranges in angles of incidence between a minimum angle of incidence, $\theta_{min}$, and a maximum angle of incidence, $\theta_{max}$. The angle of incidence is measured relative to the normal surface 1027 which is perpendicular to the prism surface 1025. In one embodiment, the critical angle $q_c$ of the prism-sample interface 1034 should be such that $\theta_{min} < \theta_c < \theta_{max}$. A unique property of the critical angle is that for all angles larger than than $\theta_c$, 100% of the light is reflected from the interface 1034 and none transmits. For angles inside of the prism 1015 that are less than $\theta_c$, some light transmits into the sample material 1020 and therefore less than 100% of the light is reflected. In other words, for all rays in the beam of light generated by illumination lens 1010 that are focused in the prism to an incident angle greater than the critical angle $\theta_c$, 100% of the light is reflected off of the prism-material interface 1034 and propagates towards the collection lens 1030 and then on to the linear detector 1035 or photodetector. The light ray that is incident upon the prism-sample interface 1034 at $\theta_c$ will strike the linear detector 1035 at a point $x=x_c$. By analyzing the detected light levels from $x=0$ to $x=x_{max}$ on the detector 1035, the firmware 1047 or software of the refractometer detects the position $x_c$ since for $x_c < x < x_{max}$, the light level is substantially constant across the detector array 1035. With a well-calibrated refractometer, the detector position $x_c$ is mapped back to a critical angle $\theta_c$, which from EQUATION 8 below and knowing the index of refraction of the prism $n_p$, the index of refraction $n_s$ of the sample can be determined and displayed or otherwise reported.

$$\theta_c = \arcsin(n_s/n_p)$$  Equation 8

Therefore, in refractometer 1000 the index of refraction of the prism 1015 must satisfy $n_p > n_s$ for all values of $n_s$ desired to be measured in order for a critical angle $\theta_c$ to exist. Given the range of $\theta_c$ resulting from the range of $n_s$ to be measured, the illumination lens 1010 arrangement is designed to include this range of angles relative to the surface normal 1027 of surface 1025. Similarly, the collection lens 1030 is designed such that the range of angles $\theta_c$ are linearly mapped to positions x on the linear detector array 1035. By way of example, for a refractometer designed to operate with a sugar solution between 0 and 10° BRIX at 20° C., one requires the ability to detect indices of refraction ranging from 1.3330 to 1.3479. Using a source with a wavelength of $\lambda_0 = 589$ nm and a prism made of BK7 ($n_p = 1.5167$ @$\lambda_0$), the range of critical angles to detect are $\theta_c = 61.50°$ to 62.71°. Choosing an Eastman Kodak (Rochester, N.Y.) linear CCD array model KLI-2113 with an array of 2098 pixels for linear detector 1035, the theoretical resolution is 7E-6 in index of refraction and 0.005° BRIX. In addition to being wavelength sensitive, the index of refraction for any material changes slightly with temperature. For water at 20° C. (68° F.) the index of refraction is 1.333 and changes by −0.0001 for every degree C. The disclosed coffee refractometer includes automatic temperature compensation as described in more detail below.

Refractometer 1000 includes a microcontroller 1045 with control firmware 1047 or control software therein. Microcontroller 1045 includes a memory store 1049 for storage of information and data. Refractometer 1000 also includes a temperature sensor 1050 near the prism-sample interface 1034 of prism 1015. Temperature sensor 1050 couples to an input of microcontroller 1045 to inform microcontroller 1045 of the current temperature of the prism-sample interface 1034. A control line 1055 couples microcontroller 1045 to light source 1005 to enable microcontroller 1045 to control light source 1005. Refractometer 1000 also includes a display 1060 to allow refractometer 1000 to display measurement results such as a TDS % value of the brew sample 1020. Refractometer 1000 further includes a network interface 1065 that enables refractometer 1000 to connect via wire or wirelessly to other information handling systems 600 or the Internet 1070. Information handling system 600 may include coffee design application 602 which uses the TDS % coffee brew sample result from the refractometer 1000 as input for coffee design universal control chart display purposes.

FIG. 10B is a block diagram of a brewing station 1075 that employs the disclosed coffee design system 600 and the disclosed coffee refractometer 1000. In one embodiment, coffee brewing station 1075 includes a hot water supply 1076 and a brew basket assembly 1077 where coffee grounds mix with hot water to form a coffee drink. As the coffee drink exits brew basket 1077, the coffee drink flows downward into a vessel 1078 that captures the brewed coffee. Vessel 1078 dispenses brewed coffee to coffee pot 1079 or other container suitable for transporting of the brewed coffee to the coffee drinker. In one embodiment, a coffee refractometer 1000 is situated in vessel 1077 so that refractometer 1000 may determine the TDS reading of a freshly brewed batch of coffee immediately after brewing. A user may take a reading of the TDS % of the coffee from the display of refractometer 1000. The user may then manually input the TDS % reading into coffee design application 602 of IHS 600. In response, coffee design application 602 displays the actual TDS % and extraction on the plotted brew line of a universal brew line chart such as seen in FIG. 5. In an alternative embodiment shown in FIG. 10B, refractometer 1000 couples to, or otherwise communicates with IHS 600. In this manner, refractometer 1000 reads and supplies TDS % data to coffee design application 602 of IHS 600 without manual user intervention.

FIG. 11A is a flowchart that depicts process steps for configuring refractometer 1000 to determine the total dissolved solids (TDS) % of a brew coffee sample. To use refractometer 1000 to measure the total dissolved solids (TDS) of coffee or any other liquid, refractometer 1000 should be both calibrated and correlated. The calibration of a refractometer is performed by measuring the index of refraction of distilled pure water at a specific temperature to ensure that the refractometer is measuring index of refraction properly. The correlation of a refractometer is the conversion of the measured index of refraction to a scale of interest to the end user. Typically, refractometers have software that correlates to a BRIX scale. In that case the software assumes that the index of refraction of the liquid presented to the refractometer corresponds to a sugar-water solution and will output a BRIX value (equal to the % sugar by weight in solution) based upon the measured refractive index. Unfortunately, for most other liquids, such as coffee, a BRIX scale is not valid and can lead to erroneous results.

To configure refractometer 1000 to measure the TDS of a brewed coffee sample, process flow commences at start block 1105 in the flowchart of FIG. 11A. A user or other entity first calibrates refractometer 1000, as per block 1110. The calibration of refractometer 1000 is performed in the conventional manner by measuring the index of refraction of distilled pure water at a specific temperature to ensure that the refractometer is measuring index of refraction properly.

To correlate refractometer 1000 for coffee, the change in index of refraction with TDS as well as temperature is determined. The user or other entity begins correlation of refractometer 1000, as per block 1115. One exemplary and preferred method of determining the TDS of a coffee solution is through a dehydration method. To start the correlation procedure, different batches of coffee are brewed at different brew concentrations, while maintaining approximately the same extraction percentage from the selected batch of roasted and ground coffee beans, as per block 1120. In other words, the user or other entity brews multiple coffee samples with different respective coffee concentrations in terms of total dissolved solids (TDS) %. The extraction percentage set during the refractometer correlation procedure is preferably the extraction percentage chosen as that of an ideal coffee solution for consumption. For purposes of example, the extraction percentage is 20%±1% although it is possible to employ other extraction percentages if desired depending on the application and user preference. For an accurate correlation procedure, it is preferable that the extraction percentage remains approximately constant because coffee grinds are composed of a mix of different materials that have different water solubility rates. The materials that have a high water solubility rate are extracted first from the coffee grinds and give the coffee a sweet flavor. Those materials that have a lower water solubility rate are extracted later in the brewing process and give the coffee a bitter flavor. Each of these different materials contained within coffee affect the index of refraction of water differently when they dissolve into it. Therefore for accurate correlation of the index of refraction of coffee to TDS, it is preferred that the extraction percentage is kept approximately constant. Note further that during the described correlation procedure it is preferred that the coffee used to make the different batches of coffee concentrations are from the same green and roast batch, and further, that they are ground to the same grade. For example, all-purpose universal Drip Grind would be derived of 8% Numbers 10/14 sieves, 65% Numbers, 27% Pan for a nominal particle size of 775 Microns (1 Micron-0.001 mm), according to the North American Coffee Industry Norms as published by Modern Process Equipment, Inc.

If required, a separate correlation procedure can be conducted for each coffee bean of interest and/or different degrees of roast to determine refractometer correlation equations for these bean and roast changes. For the brew concentrations that have the same extraction percentage, it is preferred that they encompass the range of TDS expected for the consumable coffee of interest. By way of example, the brew samples can span a 0.8% to 4.0% TDS range, since 1% to 1.5% TDS represents the typical range for coffee, and 3% to 4% represents the typical range for ice coffee concentrate. For expresso, the brew concentration of 2 to 6% TDS is typically of interest with the TDS range of 4 to 5% being preferable. For expresso, given that it contains a certain percentage of undissolved solids, these solids would need to be filtered before following the dehydration procedure outlined below.

Samples of each brew concentration are allowed to cool in respective sealed vial, as per block 1125. Refractometer 1000 then measures not only the index of refraction of the sample but also the temperature of the sample. More particularly, refractometer 1000 measures the index of refraction ($n_s$) for each brew concentration sample across a range of temperatures as per block 1130. For the correlation of refractometer 1000 for use outside of the brewing machine itself, a temperature range corresponding to ranges of ambient room temperatures are preferred such as 20 to 30° C. and index of refraction measurements can, for example, be taken in 1° C. increments. For a refractometer 1000 to be used to measure the index of refraction of coffee after it is brewed, the desired temperature range may be 70 to 90° C. with measurements taken every 2° C. as part of the correlation process. These correlation measurements are useful to derive the thermal dependence of the index of refraction for a specific brew concentration (i.e., a specific TDS).

To determine the TDS of each of the brew concentrations, containers (for example, glass beakers) are marked and weighed (preferable to an accuracy of 1 part in 1000 or better), as per block 1135 ($1^{st}$ weight reading). Portions of each brewed coffee solution are poured into individual containers (not shown) and the filled containers are reweighed ($2^{nd}$ weight reading), as per block 1140. The filled containers are then placed into a dehydration oven, as per block 1145. After the solutions have been dehydrated or desiccated, the containers are allowed to cool in a dry environment in order to prevent any subsequent moisture absorption, as per block 1150. The containers are then reweighed ($3^{rd}$ weight reading) preferably in a dry environment, also as per block 1155. From these three weight readings, the weight of the dissolved solids and the weight of the original solution is derived, and therefore the TDS (equal to the ratio of these two measurements) is derived.

In more detail, assuming eight brewed samples of coffee of different TDS spanning 0.8 to 4.0% and ten temperature readings per sample, 80 data points are thus provided that map a three-dimensional space in TDS, temperature and refractive index. Taking TDS as the dependent variable, the TDS surface plot as a function of temperature and refractive index can be curve fit to find an equation that expresses TDS as a function of index of refraction (n) and temperature (T), (i.e. f(n, T)) as per block 1160. Generally speaking, the curve fit of such data will be suitably fit by a linear function in index of refraction and a quadratic function of temperature. Curve fitting methods such as least squares, gradient descent, and others methods may be used. See for example, C. Daniel and F. S. Wood, *Fitting Equations to Data: Computer Analysis of Multifactor Data*, (John Wiley & Sons, NY, N.Y.), 1980]

The TDS formula for a fixed temperature $T_0$ is given by EQUATION 9 below:

$$TDS(n, T_0) = \frac{[n(T_0) - n_0(T_0)]}{C}, \qquad \text{EQUATION 9}$$

where $n_0$ is the index of refraction at which the curve fit indicates that the TDS is zero. Note that $n_0$ may not necessarily correspond with the exact index of refraction measured for pure water. Assuming that the range of index of refraction and hence TDS is relatively small, such as is the case for normal coffee, the constant C can be approximated to be temperature independent. In order to adjust for temperatures, the thermal dependence of index of refraction should be taken into account. The thermal dependence of index of refraction n for a fixed TDS coffee solution is approximated by a quadratic equation in temperature T according to EQUATION 10 below.

$$n = n_0 + a(T - T_0) + b(T - T_0)^2 \quad \text{Equation 10}$$

where a and b are constants derived from the curve fitting of data and the index of refraction equation is expressed such that at $T=T_0$, the index of refraction is equal to $n_0$.

To the first order, the TDS formula that takes into account both index of refraction and temperature. for coffee is given by EQUATION 11 below.

$$TDS(n, T) = \frac{\left[\begin{array}{c} n - n_{01} - a_1(T - T_0) - \\ b_1(T - T_0)^2 \end{array}\right]}{C_1} \quad \text{EQUATION 11}$$

where $n_{01}$, $a_1$, $b_1$, and $C_1$ may be slightly different from the constants $n_0$, a, b, and $C_1$ of EQUATIONS. (3) and (4) depending upon the data fit.

Although EQUATION 11 may be used, for a more accurate fit of the data, particularly for higher values of TDS, it is preferred to fit the data to a full quadratic in both index of refraction n and temperature T. Although such a quadratic equation can be expressed in multiple forms that are essentially identical from the standpoint of a refractometer's electronics and/or software calculating the result, a convenient form, from the standpoint of person reading the equation is given by EQUATION 12 below.

$$TDS(n, T) = \frac{\left[\begin{array}{c} n - n_{02} + d_2(n - n_{02})^2 - \\ a_2(T - T_0) - b_2(T - T_0)^2 + \\ e_2(n - n_{02})(T - T_0) \end{array}\right]}{C_2} \quad \text{EQUATION 12}$$

since the TDS is referenced to a control temperature $T_0$ and the index of refraction of $n_{02}$, which is substantially equal to the index of refraction of pure water at a temperature $T_0$, but may deviate slightly depending upon the empirical fit of the data in the index-temperature parameter space of interest. A formula such as the one represented in EQUATION 11 or 12 is programmed into the firmware 1085 or electronics of refractometer 1000 to correlate refractometer 1000 for the liquids (e.g., coffee), concentrations, and temperatures ranges of interest. In other words, the formula of either EQUATION 11 or 12 is programmed into, installed or otherwise stored in firmware 1047 of microcontroller 1045 in refractometer 1000, as per block 1160, for use in determining TDS of a particular coffee brew sample from index of refraction data and temperature data that refractometer 1000 provides. Storing the TDS formula of EQUATION 11 or 12 in refractometer 1000 in this manner completes the correlation of refractometer 100 for coffee solutions of interest. In EQUATION 11, TDS (n,T) varies linearly with index of refraction, but is a quadratic function of temperature. EQUATIONS 11 or 12 provide respective polynomial expressions that approximate or represent TDS(n,T). In EQUATION 11, TDS (n,T) varies linearly with index of refraction but is a quadratic function of temperature. EQUATION 11 provides a polynomial expression that approximates or represents TDS (n,T). In EQUATION 12, TDS (n,T) varies as a quadratic function of index of refraction and also as a quadratic function of temperature. EQUATIONS 11 and 12 both provide a polynomial expression that approximates or represents TDS(n,T).

It should be noted that the previously cited equations are at a specific measurement wavelength since index of refraction of all materials, including coffee, will vary with the incident wavelength. Typically this wavelength is at or near the Sodium D line of 589 nm. However, other fixed wavelengths are acceptable as well.

It is also noted that different coffee varieties, different degree of roasts, different levels of extraction during brew, extraction temperatures, and other brew variables can all affect the correlation to a small degree, such that some correlations of refractive index to brew solids may result in a better fit for darker versus lighter roasts. Separate scales for each range of degree of roasts may be correlated using Agtron or similar methods for determining the degree of roast.

Microcontroller 1045 uses temperature sensor 1050 to determine and/or set the temperature of both the prism 1015 and the sample 1020. Although not shown in FIG. 10A, microcontroller 1045 may control a resistive heater and thermo-electric cooler designed to bring the sample touching the prism face to a desired temperature. Since index of refraction changes with temperature and typically in a non-linear fashion, it is desirable to compensate for temperature effects. As such, in the design of the refractometer 1000, it is desirable that the angles of incidences of the illumination beam at the entrance face of the prism and of the reflected beam at the exit face be minimized or at least compensated thermally since refraction at these interfaces will be a function of temperature. Likewise, the focal lengths of illumination lens 1010 and collection lens 1030 are a function of wavelength and to thermally compensate the temperature-dependent optical power, the lenses are preferably mounted to a mechanical mount whose thermal expansion compensates for the changes in the optical power of the lenses. Residual thermal changes to the refractometer's ability to measure index of refraction can be compensated using a lookup table based upon the readout of the temperature sensor 1050 that adds a correction factor to the critical angle detected by the refractometer.

To increase the resolution of refractometer 1000, the operating index of refraction range can be reduced and the number of detector pixels increased. Above, as a clarifying example, a refractometer was described that worked for a range of sugar solutions of 0 to 10° BRIX using an Eastman Kodak KLI-2113 linear CCD with 2098 pixels. The resolution for this example was stated as 1.4E-5 in index of refraction and 0.0095° BRIX. If instead, an Eastman Kodak Model KLI-8023 linear CCD having a length of 8002 pixels and the BRIX scale desired were reduced to 0 to 5° BRIX, the resolution can be improved by a factor of 7.6 to 1.8E-6 in index of refraction and 0.0013° BRIX. In an alternate embodiment the linear detector is not increased in size and in fact may be reduced in array size. To achieve a higher resolution the detector is scanned along the beam produced by illumination lens 1030 in order to locate the beam intensity transition point representing the critical angle. In order to properly read out the critical angle, the scanning detector should be mounted to an encoder to that its position is known.

Figure 11B:
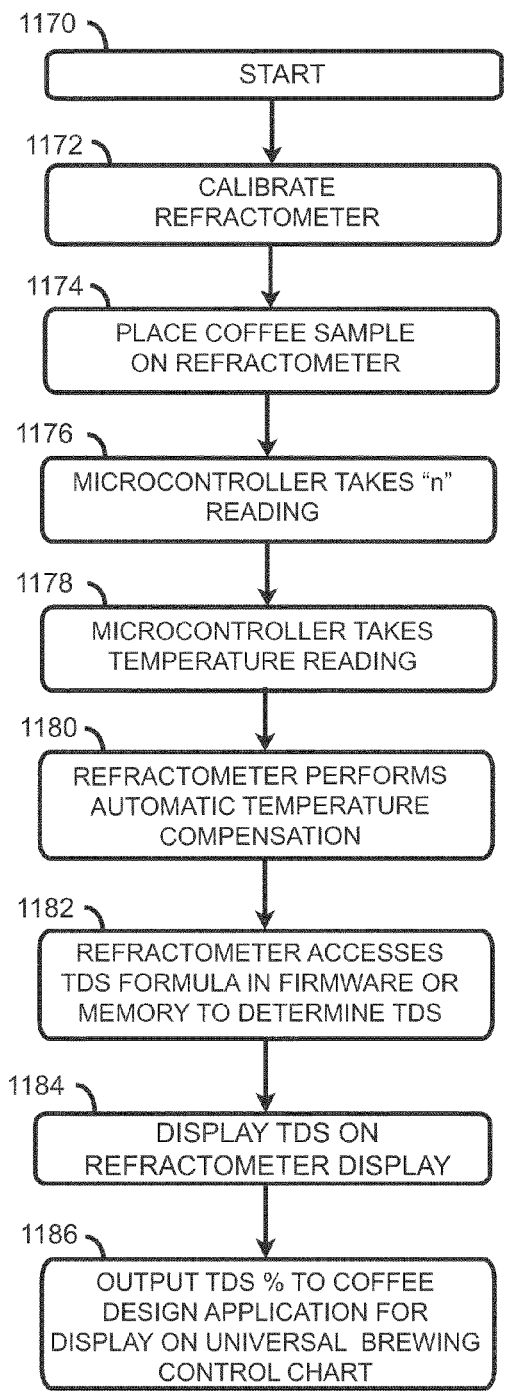
FIG. 11B is a flowchart that depicts process steps in operating the disclosed coffee refractometer to read the TDS of a coffee brew sample.

FIG. 11B is a flowchart that describes process steps that refractometer 1000 employs to take a TDS reading for a brewed coffee sample. Process flow commences at start block 1170. The user or other entity may calibrate refractometer 1000, as per block 1172. The user or other entity may place a brewed coffee sample in refractometer 1000 for the purpose of taking a TDS % reading via index of refraction measure. Refractometer 1000 takes an index of refraction reading of the brewed coffee sample, as per block 1176, under the control of firmware 1047. Microcontroller 1045 reads data from the light received by linear detector 1035 to determine the index of refraction of the brew coffee sample. In one embodiment, microcontroller 1045 of refractometer 1000 takes a temperature reading of the prism-sample interface 1034, as per block 1178. Refractometer 100 provides automatic temperature compensation for index of refraction readings of brew coffee samples, as per block 1180. Refractometer 1000 accesses the TDS formula of EQUATION 11 or 12 that firmware 1047 or memory 1049 stores to determine the TDS % of the brewed coffee sample, as per block 1182. Refractometer 1000 displays the determined TDS % for the brewed coffee sample on refractometer display 1060, as per block 1184. Conveniently, refractometer 1000 provides a TDS % reading directly to the user via display 1060. Refractometer 1186 then sends the determined TDS % to coffee design application 602 in information handling system 600 for display on the universal brewing control chart, as per block 1186.

As discussed above, refractometer 1000 includes a network interface 1065 that couples to the Internet either by wire or wirelessly, and that may also coupled to another IHS 600 either by wire or wirelessly. In this manner, IHS 600 or another IHS on the Internet may provide updating to onboard firmware 1047 in refractometer 1000. Refractometer 1000 may also receive updated or new scales via the Internet or IHS 600 in this manner. Refractometer 1000 may employ a wired or wireless connection to send information and data to coffee design application 602 in IHS 600 in this manner.

Those skilled in the art will appreciate that the various structures disclosed can be implemented in hardware or software. Moreover, the methodology represented by the blocks of the flowcharts of FIG. 9A-9B may be embodied in a computer program product, such as a media disk, media drive or other media storage such as computer program product medium 608 of FIG. 6A.

In one embodiment, coffee design application 602 implements the disclosed methodology as a set of instructions (program code) in a code module which may, for example, reside in the system memory 620 of IHS 600 of FIG. 6A. Until IHS 600 requires this set of instructions, another memory, for example, non-volatile storage 645 such as a hard disk drive, or a removable memory such as an optical disk or floppy disk, may store this set of instructions. IHS 600 may also download this set of instructions via the Internet or other computer network. Thus, a computer program product may implement the disclosed methodology for use in a computer such as IHS 600. In such a software embodiment, RAM or system memory 620 may store code that carries out the functions described in the flowchart of FIG. 9A-9B while processor 610 executes such code. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the required method steps. In the context of this document, a computer program product or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of determining the total dissolved solids (TDS) in brewed coffee, comprising:
   providing a brewed coffee sample to a coffee refractometer;
   determining, by the coffee refractometer, the index of refraction ($n_s$) of the brewed coffee sample;
   determining, by the coffee refractometer, the temperature of the brewed coffee sample to provide temperature compensation to the coffee refractometer; and
   accessing, by a processor in the refractometer, a memory store in the refractometer, the memory store including a TDS formula that expresses the TDS of brewed coffee as a function of the index of refraction ($n_s$) of brewed coffee and the temperature of brewed coffee, to determine the resultant TDS of the brewed coffee sample.

2. The method of claim 1, wherein the TDS formula expresses TDS as a linear function of index of refraction ($n_s$) of the brewed coffee sample and a quadratic function of the temperature of the brewed coffee sample.

3. The method of claim 1, wherein the TDS formula expresses TDS as a quadratic function of index of refraction ($n_s$) of the brewed coffee sample and a quadratic function of the temperature of the brewed coffee sample.

4. The method of claim 1, wherein the coffee refractometer displays the resultant TDS of the brewed coffee sample on a display of the TDS.

5. The method of claim 1, further comprising transmitting, by the refractometer, the resultant TDS to a coffee design application in an information handling system for display as an actual TDS value on a universal brewing control chart.

6. The method of claim 1, further comprising reducing an index of refraction range of the refractometer from a first range to a second range that is smaller than the first range to effectively increase resolution of the refractometer.

7. The method of claim 6, wherein the reducing spreads more index of refraction information across a surface of a photodetector in the refractometer.

8. The method of claim 1, wherein the refractometer couples by wire or wirelessly to another information handling system to receive firmware upgrades therefrom.

9. A coffee refractometer comprising:
   a prism for receiving a brewed coffee sample thereon to form a prism-sample interface;

a processor that controls a light source to provide incident light to the prism-sample interface, the prism-sample interface refracting light toward a photodetector that couples to the processor;

a temperature sensor, situated adjacent the prism-sample interface and coupled to the processor, that provides temperature information to the processor; and a memory store, accessible by the processor, that stores a total dissolved solids (TDS) formula that expresses the TDS of brewed coffee as a function of the index of refraction ($n_s$) of brewed coffee and the temperature of brewed coffee, to determine the resultant TDS of the brewed coffee sample.

10. The coffee refractometer of claim 9, wherein the TDS formula expresses TDS as a linear function of index of the refraction ($n_s$) of the brewed coffee sample and a quadratic function of the temperature of the brewed coffee sample.

11. The coffee refractometer of claim 9, wherein the TDS formula expresses TDS as a quadratic function of index of the refraction ($n_s$) of the brewed coffee sample and a quadratic function of the temperature of the brewed coffee sample.

12. The coffee refractometer of claim 9, further comprising a display, coupled to the processor, that displays the resultant TDS of the brewed coffee sample.

13. The coffee refractometer of claim 8, further comprising a network interface coupled to the processor that transmits the resultant TDS to a coffee design application in an information handling system (IHS) for display as an actual TDS value on a universal brewing control chart.

14. The coffee refractometer of claim 9, that reduces an index of refraction range of the refractometer from a first range to a second range that is smaller than the first range to effectively increase resolution of the photodetector.

15. The coffee refractometer of claim 14, wherein reducing the index of refraction range of the photodetector spreads a smaller range of index of refraction information across a larger surface of the photodetector.

16. The coffee refractometer of claim 13, wherein the network interface couples by wire or wirelessly to another information handling system to receive firmware upgrades therefrom or output readings in response to requests for measurements automatically another information handling system.

\* \* \* \* \*